United States Patent
Yu et al.

(10) Patent No.: US 9,404,090 B2
(45) Date of Patent: Aug. 2, 2016

(54) ADENOVIRUS PRODUCING NOVEL CELL LINE AND THE USE THEREOF

(71) Applicant: VIROMED CO., LTD., Seoul (KR)

(72) Inventors: Seung Shin Yu, Seoul (KR); Chang-Wan Joo, Seoul (KR); Jin-A Chae, Seoul (KR); Yeon Suk Cha, Seoul (KR)

(73) Assignee: VIROMED CO., LTD., Seoul (KR)

( * ) Notice: Subject to any disclaimer, the term of this patent is extended or adjusted under 35 U.S.C. 154(b) by 0 days.

(21) Appl. No.: 14/360,195

(22) PCT Filed: Nov. 22, 2012

(86) PCT No.: PCT/KR2012/009931
§ 371 (c)(1),
(2) Date: May 22, 2014

(87) PCT Pub. No.: WO2013/077645
PCT Pub. Date: May 30, 2013

(65) Prior Publication Data
US 2014/0308704 A1 Oct. 16, 2014

(30) Foreign Application Priority Data
Nov. 24, 2011 (KR) .................. 10-2011-0123654

(51) Int. Cl.
| | | |
|---|---|---|
| *C12P 21/00* | (2006.01) | |
| *C12N 15/86* | (2006.01) | |
| *C12N 7/00* | (2006.01) | |
| *C12N 5/16* | (2006.01) | |
| *C12N 15/12* | (2006.01) | |
| *C12N 15/13* | (2006.01) | |
| *C12N 5/10* | (2006.01) | |

(52) U.S. Cl.
CPC *C12N 7/00* (2013.01); *C12N 15/86* (2013.01); *C12P 21/00* (2013.01); *C12N 2710/10351* (2013.01)

(58) Field of Classification Search
None
See application file for complete search history.

(56) References Cited

U.S. PATENT DOCUMENTS

| 5,976,845 A | 11/1999 | Mezes et al. | |
|---|---|---|---|
| 2005/0003506 A1* | 1/2005 | Li et al. | 435/235.1 |
| 2006/0270041 A1* | 11/2006 | Howe et al. | 435/456 |

FOREIGN PATENT DOCUMENTS

| KR | 10-0449181 B1 | 1/2005 | |
|---|---|---|---|
| KR | 10-2007-0103483 A | 10/2007 | |
| WO | WO-99/55831 A2 | 11/1999 | |
| WO | WO-2005/010146 A2 | 2/2005 | |
| WO | WO-2006/065827 A2 | 6/2006 | |
| WO | WO 2006/113214 A2 * | 10/2006 | A61K 39/145 |
| WO | WO-2006/113214 A2 | 10/2006 | |

OTHER PUBLICATIONS van Olphen et al., "Characterization of Bovine Adenovirus Type 3 E1 Proteins and Isolation of E1-Expressing Cell Lines" 295 Virology 108-118 (2002).*
Amalfitano et al., "Production and characterization of improved adenovirus vectors with the E1, E2b, and E3 genes deleted," J Virol. 72(2):926-33 (1998).
International Search Report for International Patent Application No. PCT/KR2012/009931, mailed Mar. 19, 2013 (8 pages).
van Olphen et al., "Characterization of bovine adenovirus type 3 E1 proteins and isolation of E1-expressing cell lines," Virology. 295(1):108-18 (2002).

* cited by examiner

*Primary Examiner* — Nancy J Leith
(74) *Attorney, Agent, or Firm* — Clark & Elbing LLP; Susan M. Michaud

(57) ABSTRACT

The invention relates to a cell line in which an expression construct is introduced into genomic DNA, the expression construct including: (a) a promoter operable in animal cells and heterologous to adenoviruses; and (b) a modified adenovirus E1 coding gene sequence of SEQ ID NO: 32 operatively linked to the promoter. The cell line of the invention is less likely to produce a replication competent adenovirus (RCA). The adenovirus producing cell line of the invention has a low possibility of producing RCA due to homologous recombination, when compared with conventional cell lines. Therefore, this makes it possible to regulate the required amount of virus during gene therapy using the adenovirus and prevent tissue damage and toxic effects caused by overproduction of the adenovirus. Also, the cell line of the invention shows superior adenovirus producing ability, as compared with an HEK 293 cell which is one of conventional adenovirus producing cell lines.

10 Claims, 20 Drawing Sheets

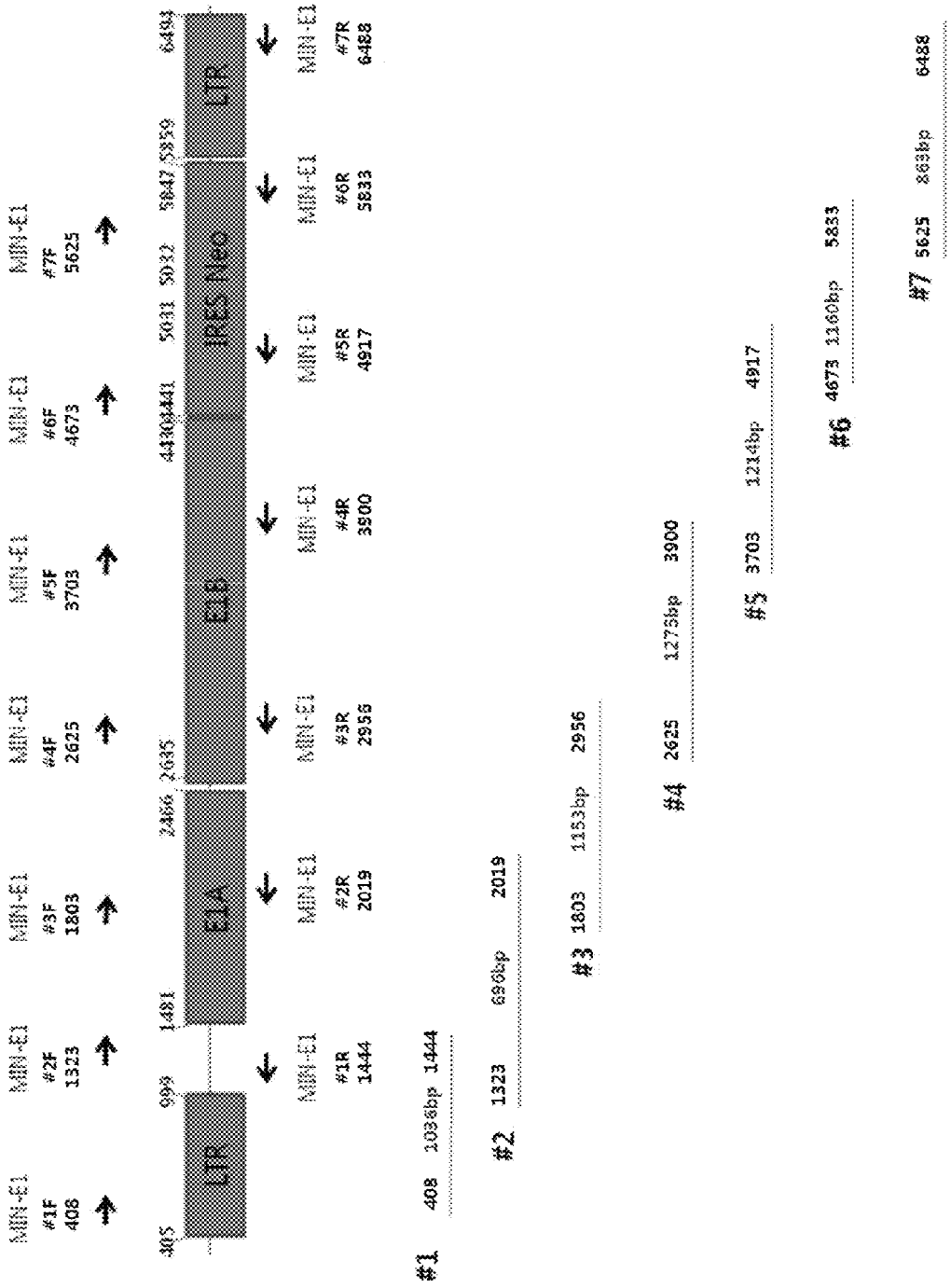

Fig. 10b

ADENOVIRUS PRODUCING NOVEL CELL LINE AND THE USE THEREOF

CROSS-REFERENCE TO RELATED APPLICATIONS

This application is the U.S. national stage filing under 35 U.S.C. §371 of international application PCT/KR2012/009931, filed Nov. 22, 2012, which claims priority from KR patent application No. 10-2011-0123654, filed Nov. 24, 2011.

TECHNICAL FIELD

The present invention relates to a novel adenovirus producing cell line and a use thereof.

BACKGROUND ART

Gene therapy is one of therapeutic methods that have been newly discovered to treat various diseases including cancers. The success of the gene therapy may be determined according to whether genes useful to treat target diseases are found and how efficiently the genes are delivered to target tissues. There are various gene delivery systems, and an adenoviral vector is currently being spotlighted as a carrier.

There are largely three reasons that adenoviruses are useful as a gene carrier: 1) the viral gene is not inserted into the host cell genome; 2) it can easily infect even non-dividing cells; and 3) it can efficiently deliver a target gene in vivo (Brody and Crystal, 1994). However, adenoviruses have one drawback regardless of the above advantages. The drawback is that replication competent adenovirus (RCA) may be produced upon production of recombinant adenoviruses.

Recombinant adenoviral vectors can be relatively easily mass-produced as compared with other virus vectors. The replication competence of the recombinant adenoviral vector can be simply lost by the deletion in early region (E1) of the viral genome. All adenoviral vectors may be this type of replication-incompetent vector. Conventionally, HEK293, a cell line having a part of the viral genome (nucleotides 1-4344), is used to construct the replication-incompetent recombinant adenoviral vector. Since E1 is crucial for the production of viruses, a cell line capable of temporarily supplying E1 is used. When the replication-incompetent adenoviruses are produced, only replication-incompetent viruses need to be produced. However, replication-competent adenoviruses may be produced due to the homologous recombination between the viral genome region except adenoviral E1 in HEK 293 cells and the viral genome region in the vector.

When the recombinant adenoviruses are produced, the production of RCA may cause the following problems: 1) the replication degree of viruses that are internally administered cannot be controlled; 2) replication-incompetent adenoviruses may be converted into replication-competent adenoviruses; and 3) the production of adenoviruses in an amount more than the amount required for gene therapy may cause tissue damage and severe toxicity. In order to solve these problems, many researchers who research recombinant adenoviral vectors have endeavored to develop adenovirus-producing cell lines capable of substituting for HEK293 cells and reducing the possibility of RCA production.

Since HEK293 cells contain considerably more regions of the adenoviral genome other than the adenovirus E1 gene, the possibility of the homologous recombination between HEK293 cells and the E1-deficient adenoviral vector may be high. Therefore, cells substituting for HEK293 cells have been developed to contain fewer regions of the adenoviral genome than HEK293 cells. During the 1990s, 911 cells were first developed as an adenovirus producing cell line. 911 cells are based on human derived retinoblasts. These cells have a part of the adenoviral genome (nucleotides 79-5789), and have excellent virus production capacity but similar RCA production capability as compared with HEK293 cells (Fallaux et al., 1996). Around the same time, an adenovirus producing cell lines using A549 cells, which are human bronchial cancer cells, were also developed. These cells were characterized by having fewer regions of the adenoviral genome (nucleotides 505-4034), and failed to be commercialized due to their poor adenoviral production capacity. PER.C6 cells are an adenovirus producing cell line that is the most widely known and commercially available, and developed based on human-derived retinoblasts like the above-described 911 cells. These cells are characterized by having fewer regions of the adenoviral genome (nucleotides 459-3510) as compared with the above-described cell lines. These cells exhibited a significant reduction in RCA production as compared with HEK293 cells. However, it has been reported that RCA was produced upon the mass production of this cell line (Murakami et al., 2004). Besides, adenovirus producing cells may be developed using human uterine cervical cancer cells, HeLa cells, but failed to be commercialized due to reasons such as, failing to significantly lower the possibility of RCA production, reducing the virus production capacity, and the like (Gao et al., 2000, Kim et al., 2001).

In order to solve the disadvantages of the above-described adenovirus producing cell lines, the present inventors have endeavored to develop adenovirus producing cell lines capable of: 1) remarkably lowering the possibility of RCA production by having fewer regions of adenoviral genome; and 2) having adenovirus production capacity superior to or similar to that of HEK293 cells.

Throughout this application, several patents and publications are referenced and citations are provided in parentheses. The disclosure of these patents and publications is incorporated into this application in order to more fully describe this invention and the state of the art to which this invention pertains.

DETAILED DESCRIPTION OF THE INVENTION

Technical Problem

The present inventors have endeavored to develop novel adenovirus producing cell lines having lowered possibility in replication-competent adenovirus (RCA) production and excellent adenovirus production capacity. As a result, the present inventors have developed cell lines having a modified E1 coding gene sequence having a specific sequence. An adenovirus producing cell line of the present invention can trans-complement E1-deficient recombinant adenovirus and reduce the possibility of RCA production due to homologous recombination by stably providing an adenovirus E1 gene (or protein expressed thereby) necessary to adenovirus production. Accordingly, the adenovirus producing cell lines of the present invention can control the amount of adenoviruses suitable for gene therapy and prevent tissue damage and toxic effects due to overproduction of adenoviruses. Further, it was confirmed that the adenovirus producing cell line of the present invention exhibits excellent adenovirus production capacity as compared with the conventional adenovirus producing cell lines, thereby producing replication-incompetent adenoviruses in a time- and cost-economical manner, and thus the present invention has been completed.

Therefore, the present invention has been made in view of the above-mentioned problems, and an aspect of the present invention is to provide a novel cell line in which introduced a modified adenovirus E1 coding gene sequence.

Another aspect of the present invention is to provide a cell line producing recombinant adenoviruses.

Another aspect of the present invention is to provide a cell line producing recombinant adenoviruses.

Another aspect of the present invention is to provide a packaging system for producing recombinant adenoviruses.

Another aspect of the present invention is to provide a method for producing recombinant adenoviruses.

Another aspect of the present invention is to provide a method for producing target protein.

Other purposes and advantages of the present disclosure will become clarified by the following detailed description of the invention, claims, and drawings.

Technical Solution

I. Cell Lines

In accordance with an aspect of the present invention, there is provided a cell line in which an expression construct is introduced into a genomic DNA, the expression construct including: (a) a promoter operable in animal cells and heterologous to adenoviruses; and (b) a modified adenovirus E1 coding gene sequence operatively linked to the promoter, wherein the modified adenovirus E1 coding gene sequence is deficient in an E1a TATA signal and an E1b polyadenylation signal from a sequence of the native E1 gene and includes an E1a coding sequence, an E1a polyadenylation signal, an E1b TATA signal, an E1b 19K coding sequence, and an E1b 55K coding sequence.

The present inventors have endeavored to develop novel adenovirus producing cell lines having lowered possibility in replication-competent adenovirus (RCA) production and excellent adenovirus production capacity. As a result, the present inventors have developed cell lines having a modified E1 coding gene sequence having a specific sequence. An adenovirus producing cell line of the present invention can trans-complement E1-deficient recombinant adenovirus and reduce the possibility of RCA production due to homologous recombination by stably providing an adenovirus E1 gene (or protein expressed thereby) necessary to adenovirus production. Accordingly, the adenovirus producing cell lines of the present invention can control the amount of adenoviruses suitable for gene therapy and prevent tissue damage and toxic effects due to overproduction of adenoviruses. Further, it was confirmed that the adenovirus producing cell line of the present invention exhibits excellent adenovirus production capacity as compared with the conventional adenovirus producing cell lines, thereby producing replication-incompetent adenoviruses in a time- and cost-economical manner.

According to the present invention, the cell line includes an expression construct which is introduced into a genomic DNA, the expression construct includes (a) a promoter operable in animal cells and heterologous to adenoviruses; and (b) a modified adenovirus E1 coding gene sequence operatively linked to the promoter.

A native E1 gene sequence is not modified (for example, a deletion or a mutation of nucleotides), the native E1 gene sequence includes an E1a TATA signal and an E1b polyadenylation signal (polyA), and an E1b TATA signal and an E1b polyA signal.

According to the modified adenovirus E1 coding gene sequence strategy of the present invention, the modified sequence lacks an E1a TATA signal and an E1b polyA signal.

Furthermore, the modified adenovirus E1 coding gene sequence includes an E1a coding sequence, an E1a polyadenylation signal, an E1b TATA signal, an E1b 19K coding sequence, and an E1b 55K coding sequence.

One of the features of the present invention, the modified adenovirus E1 coding gene sequence is used. Preferably, the modified adenovirus E1 coding gene sequences derived from an denovirus type 5 gene is used. More preferably, the modified adenovirus E1 coding gene sequences of SEQ ID NO: 32 derived from an adenovirus type 5 gene is used.

SEQ ID NO: 32 is an E1 gene coding sequences of human adenovirus serotype 5 (NCBI Accession Number: AY339865), the E1 coding gene sequence of SEQ ID NO: 32 includes $560^{th}$-$3509^{th}$ nucleotides among a whole genome sequence of human adenovirus serotype 5.

The modified adenovirus E1 coding gene sequences can produce a functional E1 protein, and this modified sequence is a transform of a natural-occurring E1 gene to minimize the homologous recombination with a recombinant adenovirus vector used hereinafter.

The modified adenovirus E1 coding gene sequences used in this invention may include substantially identical or substantially similar sequences to SEQ ID NO: 32. The substantial identity includes sequences with at least 80% identity, more preferably at least 90% identity and most preferably at least 95% identity as measured using one of the sequence comparison algorithms where the modified adenovirus E1 coding gene sequences is aligned with a sequence in the maximal manner.

The substantial similarity includes deletion or insertion of one or more base in the modified E1 coding gene sequence to minimize the homologous recombination with the recombinant adenoviral vector. Therefore, Accordingly, the modified E1 coding gene sequence is not limited to SEQ ID NO: 32, including sequences substantially not affecting to an activity of final products.

According to the present invention, the expression construct includes a promoter which operable in animal, preferably, mammalian cells.

According to the present invention, the promoter includes the promoters derived from the genome of mammalian cells or from mammalian viruses, for example, MLV (Murine Leukemia Virus) LTR (Long terminal repeat) promoter, CMV (Cytomegalovirus) promoter, the adenovirus early promoter, the adenovirus late promoter, the vaccinia virus 7.5K promoter, SV40 promoter, HSV tk promoter, RSV promoter, EF1 alpha promoter, metallothionein promoter, beta-actin promoter, human IL-2 gene promoter, human IFN gene promoter, human IL-4 gene promoter, human lymphotoxin gene promoter, human GM-CSF gene promoter, human phosphoglycerate kinase (PGK) promoter and mouse phosphoglycerate kinase (PGK) promoter, but not limited to. Preparably, the promoter is MLV LTR promoter.

According the expression construct, the modified adenovirus E1 coding gene sequences is operatively linked to a promoter. The term "operatively linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

According to a preferred embodiment, the expression construct additionally includes a selection marker-coding nucleotide sequence. The expression of the present invention may additionally include a antibiotics resistance gene, reporter gene (for example, GFP[green fluorescence protein], luciferase and β-glucuronidase) as a selective marker. The antibiotics resistance gene includes a antibiotics resistance gene used in the art, for example, ampicillin, gentamicin, carbenicillin, chloramphenicol, streptomycin, kanamycin, geneticin, neomycin or tetracycline may be included. Preferably, the antibiotics resistance gene is neomycin. The selective marker can be expressed by an expression system linked to an additional promoter or IRES (internal ribosome entry site). The IRES is a regulatory sequence derived from several viruses or RNAs of cells (McBratney et. al. *Current Opinion in Cell Biology* 5:961(1993)).

According to a preferred embodiment, the expression construct includes MLV 5'-LTR, the modified E1 coding gene sequence of SEQ ID NO:32, the selection marker-coding nucleotide sequence and MLV 3'-LTR in the 5'→3' direction. More preferably, the expression construct includes MLV 5'-LTR, the modified E1 coding gene sequence of SEQ ID NO:32, IRES, the antibiotics resistance gene and MLV 3'-LTR in the 5'→3' direction.

A cell tranfected the expression construct includes various cells, preferably, A549 (Carcinomic Human Alveolar Basal Epithelial Cell), HER (Human Embryonic Retinoblast), HeLa (Human Cervical Cancer Cell), CHO (Chinese Hamster Ovary Cell), BHK (Baby Hamster Kidney Cell), africa green monkey kidney cell, cockerspaniel kidney cell, 3T3 (Mouse Embryonic Fibroblast Cell), myeloma, PC12 (Rat Pheochromocytoma Cell), human amniocyte), WS1 (Human Dermal Fibroblast), MRC5 (Human Lung Fibroblast) or WI38 (Human Lung Fibroblast Cell). More preferably, the cell used in the present invention is Hela.

One or several expression constructs can be inserted to genomic DNA, preferably, the cell line has genomic DNA in which included one copy of expression construct.

Adenovirus is non-enveloped, icosahedral virus which is 60-90 nm in size. Currently, 51 human adenovirus serotypes have been identified which may be classified into six subgroups (A, B, C, D, E and F) according to hemagglutination properties and sequence homology relationship (Francki et al. 1991, EP 978566). Among these, adenovirus type 5 of subgroup C is a suitable starting material, and genetic information of adenovirus type 5 is well-known. According to the present invention, Early region-1(E1) gene of human adenovirus type 5 is used.

The adenovirus infectious cycle can be clearly defined into two phase. The first phase covers the entry of the virus into the host cell, followed by the virus DNA replication. The second phase starts with the initiation of viral replication. In the first phase, early genetic materials coding by E1, E2, E3, E4 are expressed, which functions for producing virus structural proteins (Berk, 1986). The late genetic materials is expressed in the seconde phase, at this time, the synthesis of DNA and proteins of hosts is stopped (Tooze, 1981).

The E1 gene of adenovirus is the first expressing gene, and can be subdivided into E1A and E1B. The main function of proteins expressed from E1A, 1) restarting to the DNA replication of cells which has been stopped, 2) activating the transcription of E1B and other early genes (E2, E3 and E4). The E1B gene product allows to replicate the virus by inhibiting the host protein synthesis and promoting the viral gene expression. As mentioned above, the adenovirus E1 gene is crucial in the viral replication, and the deletion of E1 gene leads to the loss of replication ability. Therefore, general recombinant adenoviral vector used in a gene therapy is deleted the E1 gene.

According to a preferred embodiment, the modified E1 coding gene of SEQ ID NO:32 can be obtained by performing PCR with suitable primers.

A retroviral vector is manufactured by including the modified E1 coding gene for obtaining the E1-included cell line which can trans-complement E1-deficient recombinant adenovirus.

The retroviral vector can induce the stable and steady expression of delivery gene, shows the high efficiency of integration ratio compared with a transfection method using a lipid family (Stevens et al., 1996).

According to a preferred embodiment, the retroviral vector has none of virus coding sequences by completely removing gag, pol, and env genes from a retroviral vector derived from murine leukemia virus and has no risk of homologous recombination, which is a problem of the conventional retroviral vector. The present inventors has been investigated the efficiency of the retroviral vector, and published these result to international journals (Yu et al., 2000, Yu et al., 2003, Kang et al., 2011).

In order to construct a retroviral vector, the modified E1 coding gene sequence of the invention is inserted into the viral genome in the place of certain viral. To produce virions, a packaging cell line containing the gag, pol and env genes is constructed. When a recombinant plasmid containing the modified E1 coding gene sequence of the invention, LTR and Ψ is introduced into this cell line, the Ψ sequence allows the RNA transcript of the recombinant plasmid to be packaged into viral particles, which are then secreted into the culture media (Nicolas and Rubinstein "Retroviral vectors," In: Vectors: A survey of molecular cloning vectors and their uses, Rodriguez and Denhardt (eds.), Stoneham: Butterworth, 494-513(1988)). The media containing the recombinant retroviruses is then collected, optionally concentrated and used for gene delivery.

The retrovirus may have a suitable envelope for inducing the efficient transfection to a target cell. The envelope include any envelopes which known in the art, vesicular stomatitis virus glycoprotein (VSV-G) envelope, gibbon ape leukemia virus envelope (GaLV), feline leukemia virus envelope (FeLV) or molony murine leukemia virus (MLV) envelope. Preferably, the envelope is vesicular stomatitis virus glycoprotein envelope.

After cells are trasfected with retrovirus, the present cell line inserted the modified E1 coding gene sequence can be obtained.

According to a preferred embodiment, the cell line of the present invention is deposited under accession No. KCLRF-BP-00271, H2C16 cell line. The H2C16 cell line is derived from Hela cell, has one copy of the modified E1 coding gene of SEQ ID NO:32 in genome.

An adenovirus producing cell line of the present invention can trans-complement E1-deficient recombinant adenovirus and reduce the possibility of RCA production due to homologous recombination by stably providing an adenovirus E1 gene (or protein expressed thereby) necessary to adenovirus production, thereby producing replication-incompetent adenoviruses efficiently.

II. Cell Line

In accordance with another aspect of the present invention, there is provided a cell line producing recombinant adenoviruses, the cell line comprising an adenoviral vector in the cell line of the present invention.

A cell line producing recombinant adenoviruses of the present invention includes the adenoviral vector described hereinabove. Accordingly, the common descriptions between them are omitted in order to avoid undue redundancy leading to the complexity of this specification.

The adenoviral vector of the present invention include any adenoviral vectors which known in the art. Preferably, the adenoviral vector of the present invention is deficient in a part or all of the E1 sequence, thereby cannot produce E1 proteins or produce inactivated E1 proteins.

According to the present invention, the adenoviral vector includes 100-200 bp ITR (inverted terminal repeat), which are cis elements necessary for viral DNA replication and packaging. The adenoviral vector of the present invention includes E2 region (E2A and E2B), the expression of the E2 region results in the synthesis of the proteins for viral DNA replication. The adenoviral vector of the present invention includes E3 region or not. The deleted E3 region in adenoviral vectors may provide an insertion site for transgenes (Thimmappaya, B. et al., Cell, 31:543-551(1982); and Riordan, J. R. et al., Science, 245:1066-1073(1989)). Furthermore, a foreign gene may be inserted into the deleted E1 or E4 region. In case of E1 insertion, a suitable promoter (described above) locating E1 upstream regulates the foreign gene expression which inserted in E1 region. The term "deletion" with reference to viral genome sequences encompasses whole deletion and partial deletion as well. In nature, adenovirus can package approximately 105% of the wild-type genome, providing capacity for about 2 extra kb of DNA (Ghosh-Choudhury et al., EMBO J., 6:1733-1739(1987)). In this regard, the foreign sequences described above inserted into adenovirus may be further inserted into adenoviral wild-type genome. The foreign genes delivered by the adenoviral gene delivery system are episomal, and therefore, have low genotoxicity to host cells.

A part or all of the recombinant adenovirus of the present invention is replication-incompetent. Preferably, all of the recombinant adenovirus is replication-incompetent. As used herein, the term "all replication-incompetent" refers to an substantially replication-incompetent. For example, an adenoviral genome in the cell medium is amplified by using PCR, investigating whether E1 region is or not, if the E1 region is not detected in the PCR sensitivity level, it means "all-deficient".

For enhancing a therapeutic effect of the recombinant adenovirus, the adenoviral vector of the present invention includes additional therapeutic genes.

For example, the therapeutic genes encodes proteins having anti-tumor activity and eventually degenerating tumor cells such as tumor suppressor genes, immunomodulatory genes [e.g, cytokine genes, chemokine genes and costimulatory factor genes (for T cell activity such as B7.1 and B7.2)], antigenic genes, suicide genes, cytotoxic genes, cytostatic genes, pro-apoptotic genes, anti-angiogenic genes and aptamer, but not limited to.

The suicide genes encode proteins capable of conferring to tumor cells sensitivity to chemotherapeutic agents, or of inducing toxic conditions in tumor cells. The most well-known suicide gene is the herpes simplex virus-thymidine kinase (HSV-TK) gene (U.S. Pat. Nos. 5,631,236 and 5,601,818). Cells expressing HSV-TK are susceptible to selective cell death by gancyclovir. The tumor suppressor genes encode polypeptides to inhibit tumorigenesis. The tumor suppressor genes are inherent in mammalian cells and their deletion or inactivation is believed to be a prerequisite for tumorigenesis. Examples of the tumor suppressor genes include members of the tumor suppressor gene INK4 family, which are exemplified by APC, DPC4, NF-1, NF-2, MTS1, WT1, BRCA1, BRCA2, VHL, p53, Rb, MMAC-1, MMSC-2, retinoblastoma gene (Lee et al., Nature, 329:642(1987)), gene of adenomatous polyposis coli protein (Albertsen et al., U.S. Pat. No. 5,783,666), nasopharyngeal carcinoma tumor suppressor gene that maps at chromosome 3p21.3 (Cheng et al., Proc. Natl. Acad. Sci., 95:3042-3047(1998)), deleted in colon carcinoma (OCC) gene, MTS1, CDK4, VHL, p100Rb, p16 and p21, and and therapeutically effective fragments thereof (e.g., p56Rb, p94Rb). It will be understood that other known anti-tumor genes can be used by those of ordinary skill in the art.

The term "antigenic genes" as used herein, refers to a nucleotide sequence coding for antigenic cell surface protein which is recognized by the immune system. Examples of the antigenic genes include carcinoembryonic antigen (CEA), prostate specific antigen (PSA), α-feto protein (AFP) and p53 (WO 94/02167). In order to facilitate immune recognition, the antigenic gene may be fused to the MHC type I antigen.

The term "cytotoxic gene" as used herein, refers to a nucleotide sequence, the expression of which in a cell elicits a toxic effect. Examples of the cytotoxic genes include nucleotide sequences encoding *Pseudomonas* exotoxin, ricin toxin, *diphtheria* toxin and the like.

The term "cytostatic gene" as used herein, refers to a nucleotide sequence, the expression of which in a cell induces an arrest in the cell cycle. Examples of the cytostatic genes include, but are not limited to, p21, retinoblastoma gene, E2F-Rb fusion protein gene, genes encoding cyclin-dependent kinase inhibitors such as p16, p15, p18 and p19, growth arrest specific homeobox (GAX) gene (WO 97/16459 and WO 96/30385).

In addition, a variety of therapeutic genes useful in treating various diseases may be carried in the gene delivery system of this invention. Non-limiting examples of the therapeutic genes include genes encoding hepatocyte growth factor (HGF), cytokines (e.g., interferon-α, interferon-β, interferon-δ and interferon-γ), interleukins (e.g., IL-1, IL-2, IL-4, IL-6, IL-7, IL-10, IL-12, IL-19 and IL-20), colony-stimulating factors (e.g., GM-CSF and G-CSF), chemokine genes [monocyte chemotactic protein 1 (MCP-1), monocyte chemotactic protein 2 (MCP-2), monocyte chemotactic protein 3 (MCP-3), monocyte chemotactic protein 4 (MCP-4), macrophage inflammatory protein 1α (MIP-1α), macrophage inflammatory protein 1β (MIP-1β), macrophage inflammatory protein 1γ (MIP-1γ), macrophage inflammatory protein 3α (MIP-3α), macrophage inflammatory protein 3β (MIP-3β), chemokine (ELC), macrophage inflammatory protein 4 (MIP-4), macrophage inflammatory protein 5 (MIP-5), LD78β, RANTES, SIS-epsilon (p500), thymus and activation-regulated chemokine (TARC), eotaxin, 1-309, human protein HCC-1/NCC-2, human protein HCC-3, and mouse protein C10]. In addition, the therapeutic genes include genes encoding tissue-type plasminogen activator (tPA) or urokinase-type plasminogen activator, and LAL-generating gene to provide sustained thrombolysis for preventing hypercholesterolemia. Further, nucleotide sequences available for treatment of various diseases including cystic fibrosis, adenosine deaminase deficiency, AIDS and other infectious diseases, and malignant and inflammatory diseases are known to be useful as therapeutic genes.

The term "pro-apoptotic gene" as used herein, refers to a nucleotide sequence, the expression of which results in the programmed cell death. Examples of the pro-apoptotic genes include p53, adenovirus E3-11.6K (derived from Ad2 and Ad5) or adenovirus E3-10.5K (derived from Ad), adenovirus E4 gene, Fas ligand, TNF-α, TRAIL, p53 pathway genes and genes encoding a series of caspases.

The term "anti-angiogenic gene" as used herein, refers to a nucleotide sequence, the expression of which results in the extracellular secretion of anti-angiogenic factors. Anti-algiogenesis factors include angiostatin, inhibitors of vascular endothelial growth factor (VEGF) such as Tie 2 (PNAS, 1998, 95, 8795-8800), and endostatin.

III. A Packaging System for Producing a Recombinant Adenovirus

In accordance with another aspect of the present invention, there is provided a packaging system for producing recombinant adenoviruses, the system comprising: (a) the cell line of the present invention; and (b) an adenoviral vector.

A packaging system of the present invention includes the adenoviral vector described hereinabove. Accordingly, the common descriptions between them are omitted in order to avoid undue redundancy leading to the complexity of this specification.

Meanwhile, the packaging system for producing recombinant adenoviruses can be described by referring the description of cell lines of the present invention. The packaging system has an extracellular adenoviral vector, not intracellular, this is the difference with the cell lines for producing recombinant adenoviruses.

IV. A Method for Producing Recombinant Adenoviruses

In accordance with another aspect of the present invention, there is provided a method for producing recombinant adenoviruses, the method comprising:

(a) harvesting retroviruses from cells into which the following vectors are introduced: (i) a vector including an expression construct including a promoter operable in animal cells and heterologous to adenoviruses, and a modified adenovirus E1 coding gene sequence operatively linked to the promoter, wherein the E1 coding modification gene sequence is deficient in an E1a TATA signal and an E1b polyadenylation signal from a sequence of the native E1 gene and includes an E1a coding sequence, an E1a polyadenylation signal, an E1b TATA signal, an E1b 19K coding sequence, and an E1b 55K coding sequence; (ii) a vector including a retroviral env gene sequence; and (iii) a vector including retroviral gag and pol gene sequences;

(b) infecting cells with the retroviruses of step (a) to prepare an adenovirus producing cell line;

(c) infecting the adenovirus producing cell line of step (b) with an adenoviral vector deficient in an E1 region sequence;

(d) culturing the cell line of step (c) in a culture medium; and (e) harvesting adenoviruses from the culture medium.

A method of the present invention uses the expression construct described hereinabove. Accordingly, the common descriptions between them are omitted in order to avoid undue redundancy leading to the complexity of this specification.

Step (a): Harvest of Retroviruses

First, retroviruses are harvested from cells transfected a suitable vector.

According to the present invention, the vectors are introduced: (i) a vector including an expression construct including a promoter operable in animal cells and heterologous to adenoviruses, and a modified adenovirus E1 coding gene sequence operatively linked to the promoter, wherein the E1 coding modification gene sequence is deficient in an E1a TATA signal and an E1b polyadenylation signal from a sequence of the native E1 gene and includes an E1a coding sequence, an E1a polyadenylation signal, an E1b TATA signal, an E1b 19K coding sequence, and an E1b 55K coding sequence; (ii) a vector including a retroviral env gene sequence; and (iii) a vector including retroviral gag and pol gene sequences.

A vector is introduced into cells by various viral infection methods known in the art, such as microinjection (Capecchi, M. R., *Cell*, 22:479(1980) and Harland and Weintraub, *J. Cell Biol.* 101:1094-1099(1985)), calcium phosphate co-precipitation (Graham, F. L. et al., *Virology*, 52:456(1973) and Chen and Okayama, *Mol. Cell. Biol.* 7:2745-2752(1987)), electroporation (Neumann, E. et al., *EMBO J.*, 1:841(1982) and Tur-Kaspa et al., *Mol. Cell Biol.*, 6:716-718(1986)), liposome-mediated transfection (Wong, T. K. et al., *Gene*, 10:87 (1980) and Nicolau and Sene, *Biochim. Biophys. Acta*, 721: 185-190(1982); and Nicolau et al., Methods Enzymol., 149: 157-176(1987)), DEAE-dextran treatment (Gopal, *Mol. Cell Biol.*, 5:1188-1190(1985)), and particle bombardment (Yang et al., *Proc. Natl. Acad. Sci.*, 87:9568-9572(1990)). Preferably, calcium phosphate co-precipitation is used.

The transfected cells expresses adenovirus E1 and selection marker (such as, neomycin) at the same time.

According to a preferred embodiment, the env gene sequence of step (a) is selected from the group consisting of gene sequences coding vesicular stomatitis virus glycoprotein (VSV-G) envelope, gibbon ape leukemia virus (GaLV) envelope, feline leukemia virus (FeLV) envelope, and molony murine leukemia virus (MLV) envelope.

Step (b): Preparation of Cell Lines for Producing Adenovirus

After step (a), cells are infected with the retroviruses of step (a) to prepare a cell line for producing recombinant adenoviruses.

After retroviral infection, cells are trasfected with a certain time until the coolly forming cell clone and are screened the clone. The clone is screened by collecting as a pool of the antibiotic-resistant cells which are introduced a screening materials (e.g., antibiotics), selecting of individual clones, or both available.

According to a preferred embodiment, the Hela cell line is infected with retrovirus of step (a), incubating with neomycin-containing media, thereby producing neomycin-resistant cell line. Polybrene can be added to improve the transfection efficiency According to a preferred embodiment, retroviral vector to deliver the E1 gene is inserted into chromosome maintaining its correct structure.

Step (c): Infection of the Adenovirus

After the preparation of adenovirus producing cell lines of step (b), the cells are infected with an adenoviral vector deficient in an E1 region sequence. The adenoviral vector is as mentioned above. Preferably, the adenoviral vector includes reporter gene, such as GFP gene.

After GFP-expressing adenovirus infection of the cell line which introduced the modified E1 coding gene sequence, GFP expression is analyzed, thereby selecting the cells with a high production efficiency of adenovirus. The evaluation of the production efficiency is performed by using a fluorescent microscope, immunoblotting, fluorescence activated cell sorter (FACS), PCR or flow cytometry, but not limited to. According to one embodiment, by analyzing the relation of adenovirus production and GFP expression using FACS, the cells with a high production efficiency of adenovirus can be easily selected.

Step (d): Cultivation of the Cell line for Producing Recombinant Adenoviruses

The cell line of step (c) is cultured under the suitable condition, which is suitable for assembly and production of the recombinant adenovirus. The cell lines include all elements for assembly and production of the recombinant adenovirus. The elements for assembly and production of the recombinant adenovirus are well-known in the art (U.S. Pat. No. 5,994,128). The cell line, called a packaging cell or complement cell, produces E1-deficient recombinant adenovirus. These cells provide genetic information for producing recombinant adenoviruses.

When being other functional deficiencies in the recombinant adenovirus vectors, the packaging cell may include other additional adenovirus sequence for compensating a function of E2 or E4. These additional sequence is in genome, or non chromosomal copies such as plasmid and cosmid.

Step (e): Harvest of an Adenovirus

The adenoviruses are harvested from the medium and cells.

The adenovirus can be purified for applying to clinical trials. The adenovirus purification can be conducted by a differential centrifugation, density-gradient centrifugation (Croyle M A et al., Pharm Dev Technol 3:365-372(1998)), column chromatography (Blanche F et al., Gene Ther 7:1055-1062(2000), Huyghe B G et al., Hum Gene Ther 6:1403-1416 (1995)), expanded chromatography (Peixoto C et al, J Virol Methods 132:121-126(2006)), virus precipitation, contaminants analysis or a destruction of cell component using enzymes.

The purified adenoviruses are used of prevention and/or treatment of various diseases including gene therapy, tumor vaccination or anti-virus vaccination.

V. A Method for Producing Target Proteins

In accordance with another aspect of the present invention, there is provided a method for producing target protein, the method comprising:

(a) introducing a vector including a target protein-coding nucleotide sequence into the cell line of the present invention to obtain a transgenic cell line;

(b) culturing the transgenic cell line produced by step (a); and (c) isolating and purifying target protein produced from the transgenic cell line.

Step (a): Introduction of a Vector Including a Target Protein-Coding Nucleotide Sequence First, a vector including a target protein-coding nucleotide sequence is introduced into the cell line of the present invention.

The vector including a target protein-coding nucleotide sequence is an adenoviral vector. Adenoviral vectors are as described hereinabove. The target protein-coding nucleotide sequence can be inserted to the adenoviral vectors, such as a deleted region of E1, E3 or E4.

The vector including a target protein-coding nucleotide sequence has a structure of "promoter-target protein-coding nucleotide sequence-poly A sequence". Preferably, the "promoter-target protein-coding nucleotide sequence-poly A sequence" is inserted into the deleted E1 or E3 region of adenovirus. The target protein includes any proteins which known in the art, generally comprising biological active polypeptide, such as hormone, cytokines, interleukins, interleukins binding proteins, enzyme, antibody, growth factor, transcription regulatory factor, blood factor, vaccine, structural proteins, ligand proteins or receptors, cell surface antigen, receptor antagonist, costimulatory factor and derivates and analog thereof. More detailed, the target protein includes Gonadotropin-releasing hormone (GnRH), IL-2, IL-3, IL-4, IL-5, IL-6, IL-7, IL-8, IL-10, IL-11, IL-13, IL-15, IL-18 and their receptors, tumor necrosis factor receptor, protease activating receptor (PAR1, PAR2, PAR3, PAR4), interleukin-1 type II receptor, FMS-like tyrosine kinase (Flt3) ligand, CD40, CD39, CD30, CD27, CD134, RANKL (Receptor Activator of NF-κB ligand), RANK (Receptor Activator of NF-κB), TRAIL (Tumor necrosis factor-related apoptosis-inducing ligand), TRAIL receptor, tissue plasminogen activator, Factor VIII, Factor IX, apolipoprotein E, apolipoprotein A-I, interleukin-2 antagonist, alpha-1 antitrypsin, calcitonin, growth hormone, insulin, insulinotropin, parathyroid hormone, interferon (IFN-α, IFN-β, IFN-γ), superoxide dismutase, glucan, erythropoietin, antibodies against tumor-associated glycoprotein-72(TAG-72), glucocerebrosidase, Fc-fusion protein, globin, hematocyte growth factor (HGF), nerve growth factor (NGF), insulin-like growth factor (IGF), epidermal growth factor (EGF), fibroblast growth factor (FGF), transformation growth factor (TGF), platelet-derived growth factor (PDGF), bone-derived growth factor (BDF), colony stimulating factor, B7.1, B7.2, LIGHT, CD40L, Ox40, 4.1.BB, but not limited to. Preferably, the target protein is antibodies to the tumor-associated glycoprotein-72, more preferably, human antibodies against TAG-72.

Step (b): Cultivation of the Transgenic Cell Line

The transgenic cell line is cultured in a proper medium.

A medium useful in the step includes any conventional medium for mammalian transgenic cells culture in the art, for example, Eagles's MEM (Eagle's minimum essential medium, Eagle, H. Science 130:432(1959)), α-MEM (Stanner, C. P. et al., Nat. New Biol. 230:52(1971)), Iscove's MEM (Iscove, N. et al., J. Exp. Med. 147:923(1978)), 199 medium (Morgan et al., Proc. Soc. Exp. Bio. Med., 73:1(1950)), CMRL 1066, RPMI 1640 (Moore et al., J. Amer. Med. Assoc. 199:519(1967)), F12 (Ham, Proc. Natl. Acad. Sci. USA 53:288(1965)), F10 (Ham, R. G. Exp. Cell Res. 29:515(1963)), DMEM (Dulbecco's modification of Eagle's medium, Dulbecco, R. et al., Virology 8:396(1959)), a mixture of DMEM and F12 (Barnes, D. et al., Anal. Biochem. 102:255(1980)), Way-mouth's MB752/1 (Waymouth, C. J. Natl. Cancer Inst. 22:1003(1959)), McCoy's 5A (McCoy, T. A., et al., Proc. Soc. Exp. Biol. Med. 100:115(1959)), a series of MCDB (Ham, R. G. et al., In Vitro 14:11(1978)) and their modifications. The detailed description of media is found in R. Ian Freshney, Culture of Animal Cells, A Manual of Basic Technique, Alan R. Liss, Inc., New York, the teaching of which is incorporated herein by reference in its entity.

The general culture medium for animal cells are comprise proteins, saccharides, lipids and other various elements (foreign matter). For removing these materials, the method of the present invention can include a pre-treatment procedure. The term "pre-treatment" refers to a process for eliminating impurities before a column chromatography. By performing these processes, a culture medium volume and loads to the chromatography column can be decreased.

Step (c): Isolation and Purification of the Target Protein

After culturing the cells, target proteins produced from the transgenic cell line are isolated and purified.

The isolation and purification of target proteins can be performed by methods of ordinary skill in the art, such as ion-exchange chromatography, gel-filtration chromatography, hydrophobic chromatography or adsorption chromatography.

Advantageous Effects

Features and advantages of the present invention are summarized as follows:

(a) The present invention is directed to a novel adenovirus producing cell line capable of lowering the possibility of replication-competent adenovirus (RCA) production.

(b) The adenovirus producing cell line of the present invention has a low possibility in RCA production due to homologous recombination as compared with the conventional adenovirus producing cell lines.

(c) Since the possibility of RCA production is significantly lowered, the adenovirus producing cell line of the present invention can control the amount of adenoviruses necessary for gene therapy and prevent tissue damage and toxic effects due to overproduction of adenoviruses.

(d) Further, the adenovirus producing cell line of the present invention exhibits excellent adenovirus production capacity as compared with the conventional adenovirus producing cell line HEK293, thereby producing replication-incompetent adenoviruses in a time- and cost-economical manner.

(e) Therefore, the cell line of the present invention can efficiently produce replication-incompetent adenoviruses and provide an effective amount of adenoviruses that is safe for gene therapy.

BRIEF DESCRIPTION OF THE DRAWINGS

FIG. 9a shows expected band sizes at PCR analysis for determining the structure of the retrovirus vector and the adenovirus E1 gene that inserted to the chromosome of the selected clone (H2C16).

FIG. 10b shows SEQ ID NO: 33, a result of sequencing of all the bands for the H2C16clone. It was confirmed the sequences of all the bands were located a the B-cell translocation gene 2(BTG2) site of Chromosome 1.

MODE FOR CARRYING OUT THE INVENTION

Hereinafter, the present invention will be described in detail with reference to examples. These examples are only for illustrating the present invention more specifically, and it will be apparent to those skilled in the art that the scope of the present invention is not limited by these examples.

EXAMPLES

Example 1

Figure 1:
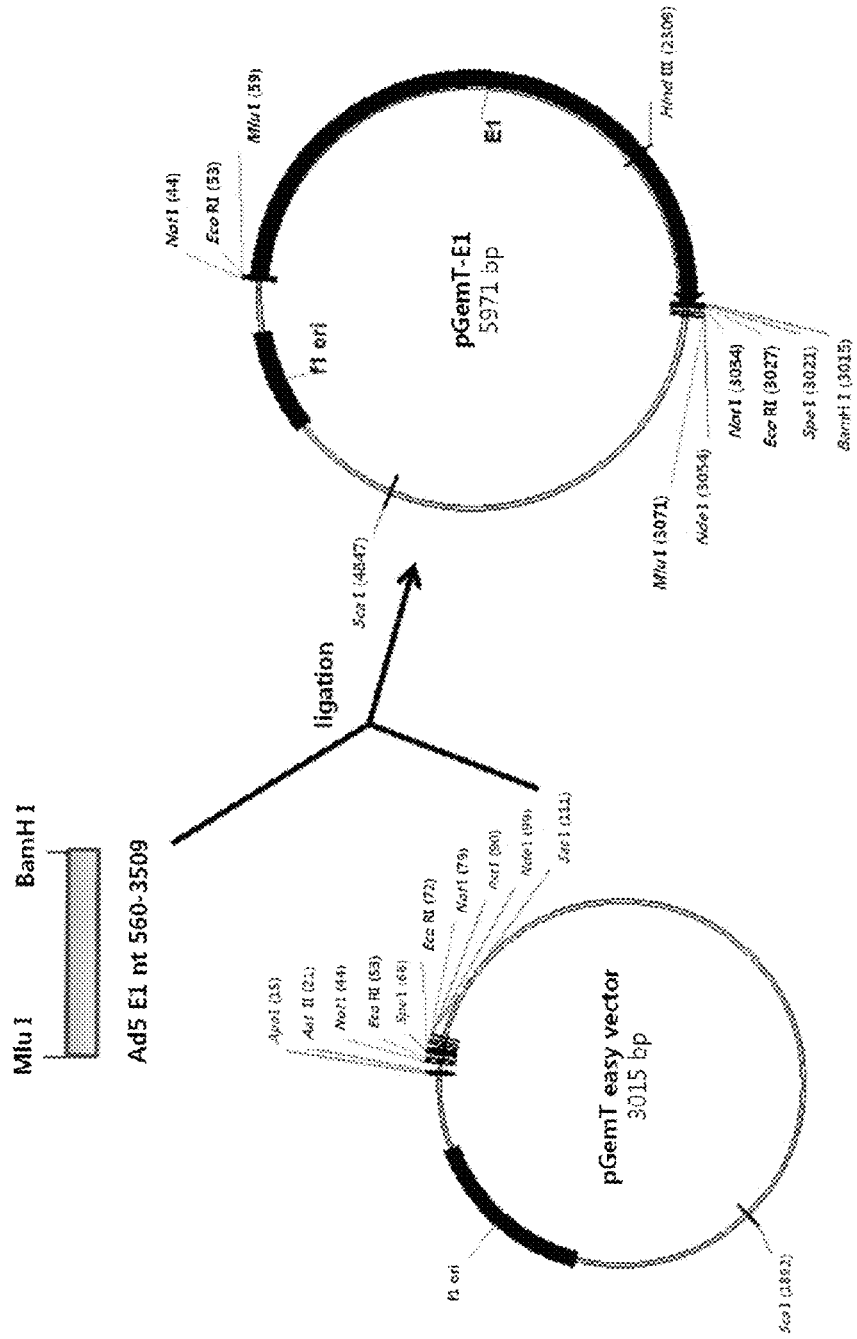
FIG. 1 is a schematic diagram showing a procedure of constructing pGem-E1 vector by securing the adenovirus type 5 E1 gene through PCR and litigating the gene to pGemT vector.

Construction of E1 Gene-Expressing Retroviral Vector 1-1. Preparation of pGemT-E1 Vector For the supply of the adenovirus E1 gene sequence, the E1 gene region of the wild-type adenovirus type 5 (Ad5) DNA, corresponding to nucleotides 560-3509, was amplified by PCR using primers of SEQ ID NO: 1 (E1-F primer, Table 1)

and SEQ ID NO: 2 (E1-R primer, Table 1). Here, since the primer bound to the 5'-region of the wild-type Ad5 DNA has the sequence of Mlu I restriction enzyme and the primer bound to the 3'-region of the wild-type Ad5 DNA has the sequence of BamH I restriction enzyme, the amplified PCR product has the sequence of Mlu I-E1-BamH I. The amplified PCR product was confirmed to be identical to the origin through sequencing, and then used for the follow-up procedure. The PCR product was ligated into the pGemT easy vector (Promega, Wis., USA) having poly T sequences at both ends of the linear DNA, thereby obtaining the structure pGemT-E1 (FIG. 1).

TABLE 1

Sequence information of used primers

| SEQ ID NO | Primer name | Sequence |
|---|---|---|
| 1 | E1-F | CCCACGCGTATGAGACATATTATCTGCCAC |
| 2 | E1-R | CCCGGATCCTCAATCTGTATCTTCATCGCT |
| 3 | HHIR | AAGCTTATGTGAAAGACCCCTCCTG |
| 4 | 5LTR3 | GGATCCGCGGGCCCACGCGTATTTTCAGACAAATACAGAAAC |
| 5 | 3LTR5 | GGATCCTCGAGGATAAAATAAAAGATTTTATTTAGTCTCC |
| 6 | 3LTR3 | GAATTCAATGAAAGACCCCCGCTGAC |
| 7 | MIN-E1 #1F | TGAAAGACCCCACCTGTAGGTT |
| 8 | MIN-E1 #1R | AGCATCGTTCTGTGTTGTCTCTGT |
| 9 | MIN-E1 #2F | TTCTGGTAGGAGACGAGAACCTAAA |
| 10 | MIN-E1 #2R | CCACAGGTCCTCATATAGCAAAG |
| 11 | MIN-E1 #3F | GTCCGGTTTCTATGCCAAAC |
| 12 | MIN-E1 #3R | GGGTTTCTTCGCTCCATTTATCC |
| 13 | MIN-E1 #4F | ATCTGACCTCATGGAGGCTTGG |
| 14 | MIN-E1 #4R | TGGAGTTACCCTCAGACAGGATA |
| 15 | MIN-E1 #5F | CCAACCTTATCCTACACGGTG |
| 16 | MIN-E1 #5R | GATCCCATACAATGGGTACC |
| 17 | MIN-E1 #6F | CCTCTGGAAGCTTCTTGAAGAC |
| 18 | MIN-E1 #6R | GTCAAGAAGGCGATAGAAGG |
| 19 | MIN-E1 #7F | GCTTGCCGAATATCATGGTG |
| 20 | MIN-E1 #7R | AAAGACCCCCGCTGACGGGTAG |
| 21 | LTR I | Biotin-AGCTGTTCCATCTGTTCCTGACCTT |
| 22 | LC I | GACCCGGGAGATCTGAATTC |
| 23 | LTR II | GACCTTGATCTGAACTTCTC |
| 24 | LC II | GATCTGAATTCAGTGGCACAG |
| 25 | LTR III | TTCCATGCCTTGCAAAATGGC |
| 26 | B19-F | ATCTGACCTCATGGAGGCTTGG |
| 27 | B19-R | GCGGACGGAAGACAGCAGTAGC |
| 28 | B55-F | GATAGATACGGAGGATAGGGTGG |

TABLE 1-continued

Sequence information of used primers

| SEQ ID NO | Primer name | Sequence |
|---|---|---|
| 29 | B55-R | TGGAGTTACCCTCAGACAGGATA |
| 30 | RCA-F | ATGAGACATATTATCTGCCAC |
| 31 | RCA-R | GTAAGTCAATCCCTTCCTGCAC |

1-2. Preparation of pMT Retroviral Vector

Figure 2:
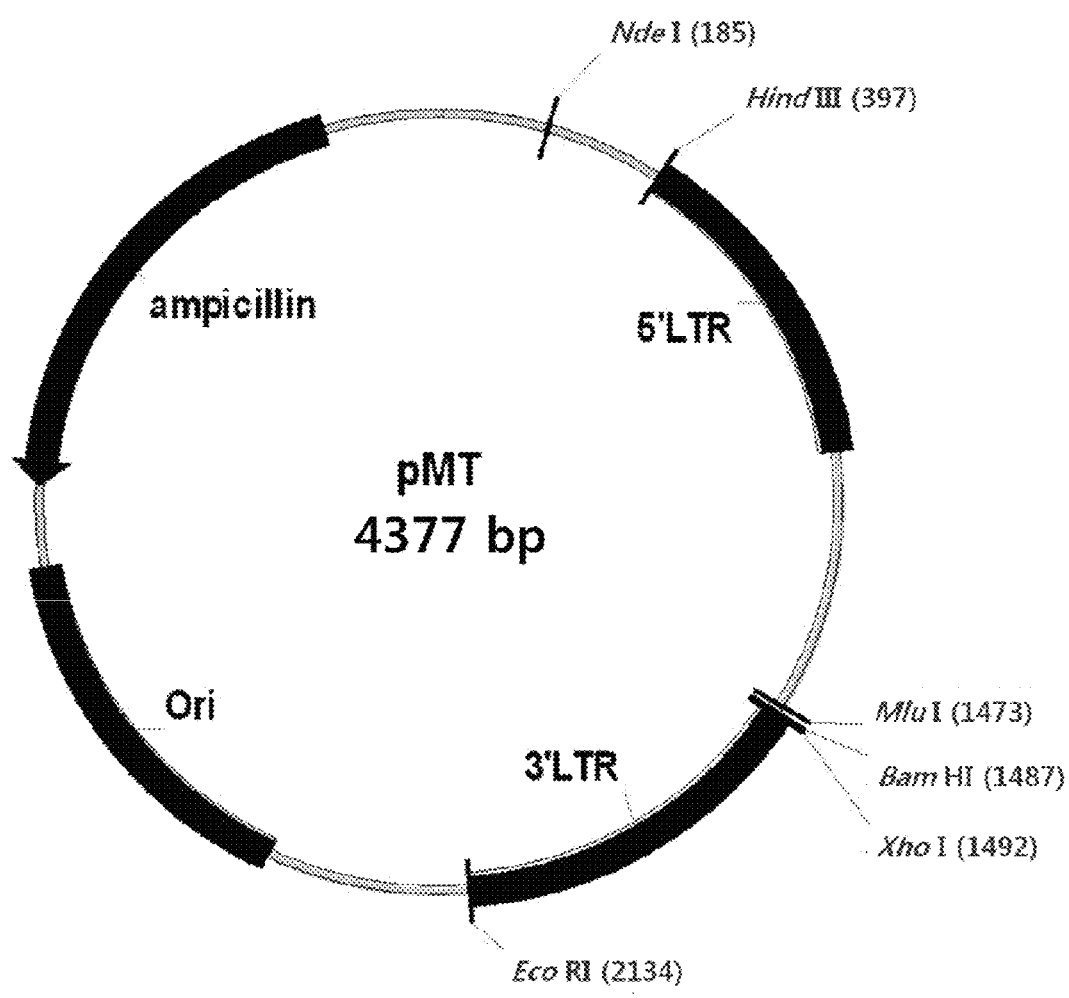
FIG. 2 is a schematic diagram showing the structure of pMT retroviral vector, which has none of virus coding sequences by completely removing gag, pol, and env genes from a retroviral vector derived from murine leukemia virus and has no risk of homologous recombination, which is a problem of the conventional retroviral vector (Yu et al., 2000).

Retroviral vector MT was prepared as follows. The nucleotide sequence necessary for the retroviral vector was amplified from the plasmid pMLV (Shinnick T M et al., 1981) having murine leukemia virus (MLV)-derived retroviral gene information by using primers of SEQ ID NO: 3 (HHIR primer, Table 1) and SEQ ID NO: 4 (5LTR3 primer, Table 1). The amplified sequence was confirmed to be identical to the origin through sequencing, and then used for the follow-up procedure. The amplified sequence includes a 5'-long terminal repeat (LTR) region of the MLV and a 5' non-coding region including a packaging signal. The thus amplified HindIII-BamHI fragment was transferred into the pUC18 vector (Invitrogen, CA, USA), thereby preparing the p5LTR plasmid vector. The 3'-LTR was also amplified from pMLV by using primers of SEQ ID NO: 5 (3LTR5 primer, Table 1) and SEQ ID NO: 6 (3LTR3 primer, Table 1). The amplified sequence includes a 3' non-coding region including a polypurine region downstream of the translation stop codon of the env gene of the MLV and 3'-LTR. The thus BamHI-EcoRI fragment was transferred into p5'LTR to prepare the pMT vector. Detailed information and functions of pMT were disclosed in an international journal (Yu et al., 2000, FIG. 2).

1-3. Preparation of pMIN Retroviral Vector

Figure 3:
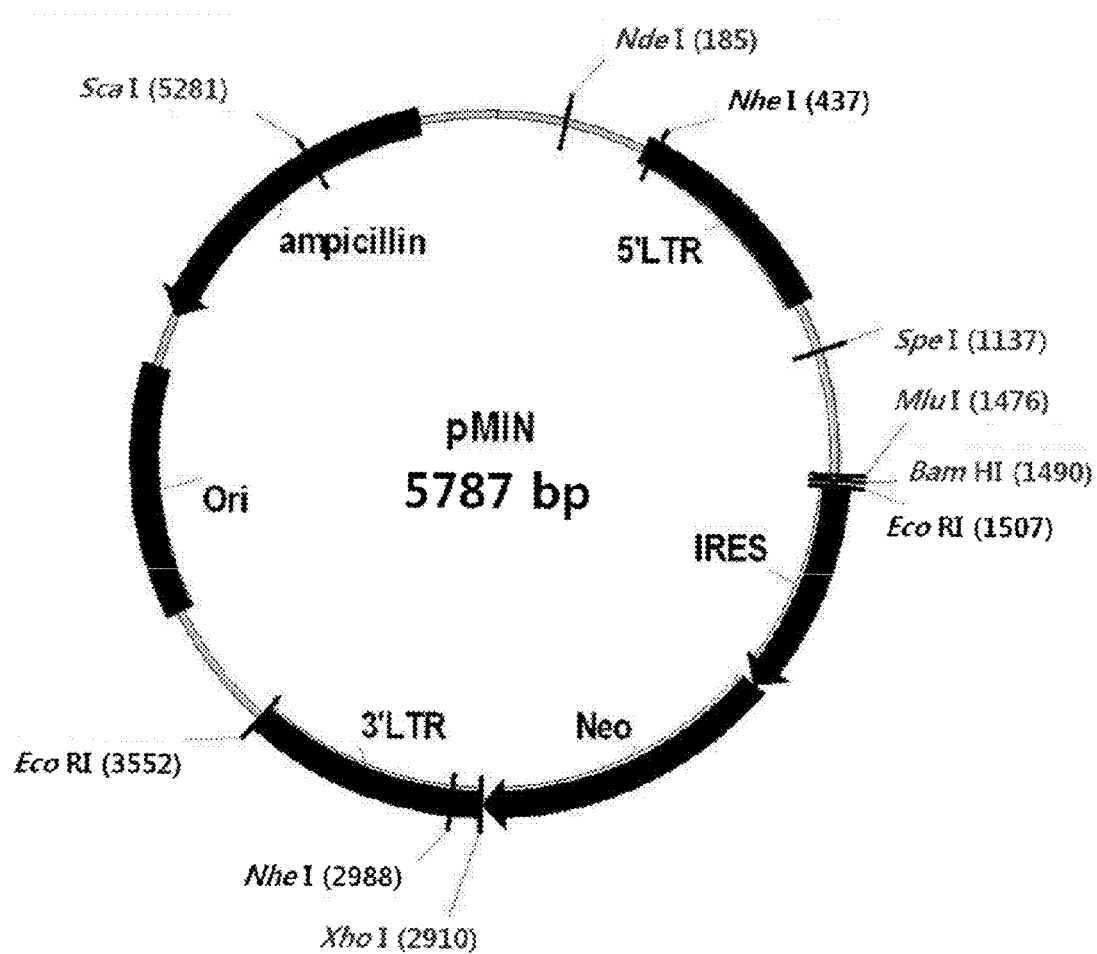
FIG. 3 is a schematic diagram showing the structure of pMIN retroviral vector in which IRES/Neo$^R$ cassette is cloned into the pMT retroviral vector.

The pCBIN (Korean Patent Application No. 1997-0048095) vector was treated with BamHI and XhoI restriction enzymes to obtain IRES/Neo$^R$ cassette. The obtained DNA fragment was litigated with the pMT retroviral vector previously treated with BamHI and XhoI restriction enzymes, to prepare pMIN retroviral vector (U.S. Pat. No. 6,451,595). When the E1 gene is inserted into the 5' region of the IRES/Neo$^R$, 5'LTR of MLV, E1 gene, IRES/Neo$^R$ cassette, and 3'LTR of MLV are constructed in that order. When this structure is delivered into the cell (as is the case where the structure in a type of viral vector is delivered into the cell and inserted into the genomic DNA of the cell), only one copy of mRNA is transcribed from the promoter in 5'LRT, which is the sole promoter in the retrovirus, and E1 protein is formed from the mRNA and Neo$^R$ protein is formed from another translation initiation site by IRES (FIG. 3).

1-4. Preparation of pMIN-E1 Retroviral Vector

Figure 4:
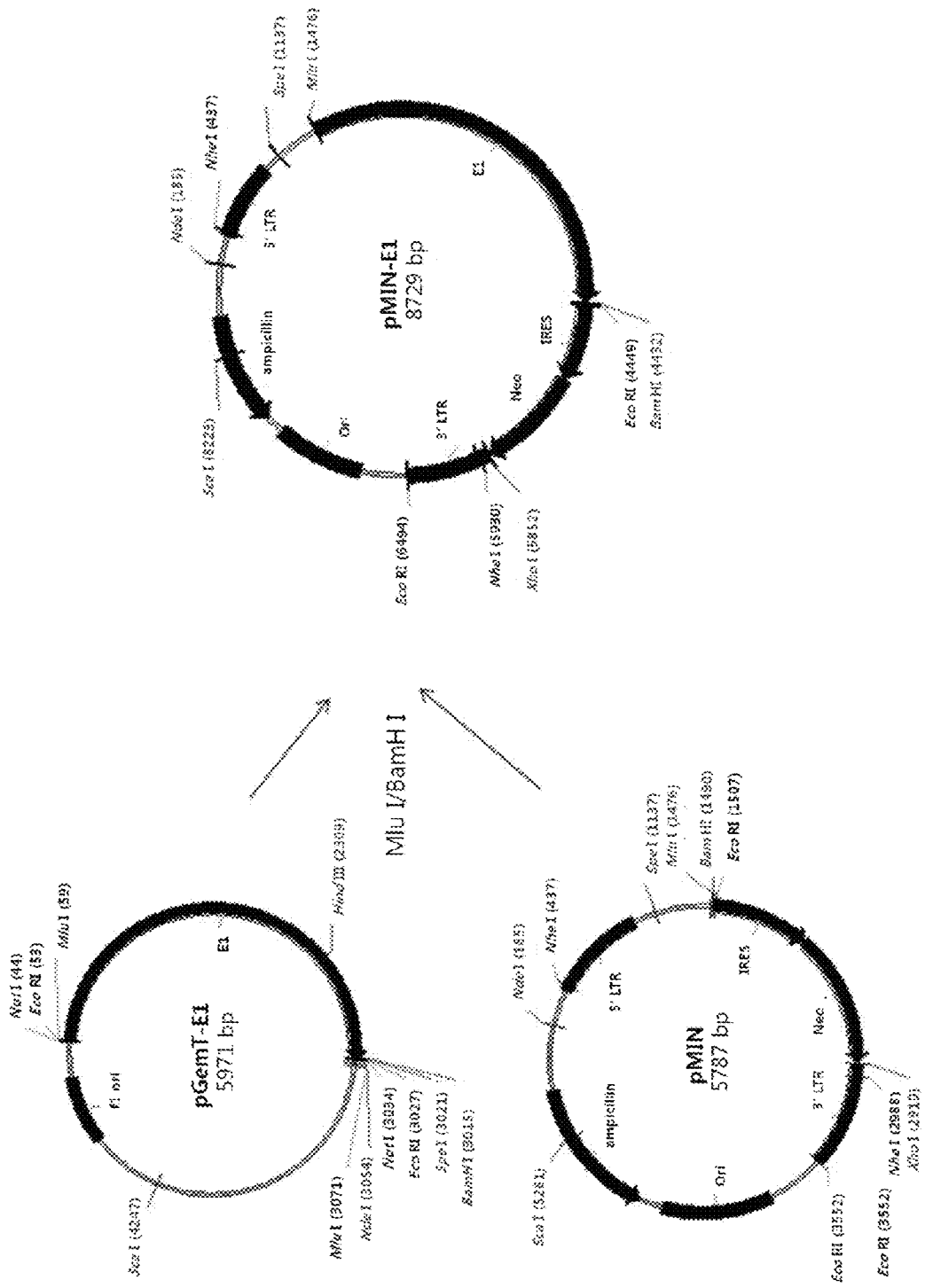
FIG. 4 is a schematic diagram showing a procedure of constructing pMIN-E1 retroviral vector by cloning an E1 gene fragment, which is obtained by treatment of pGemT-E1 with Mlu I/BamH I restriction enzymes, into the pMIN retroviral vector.
Figure 5:
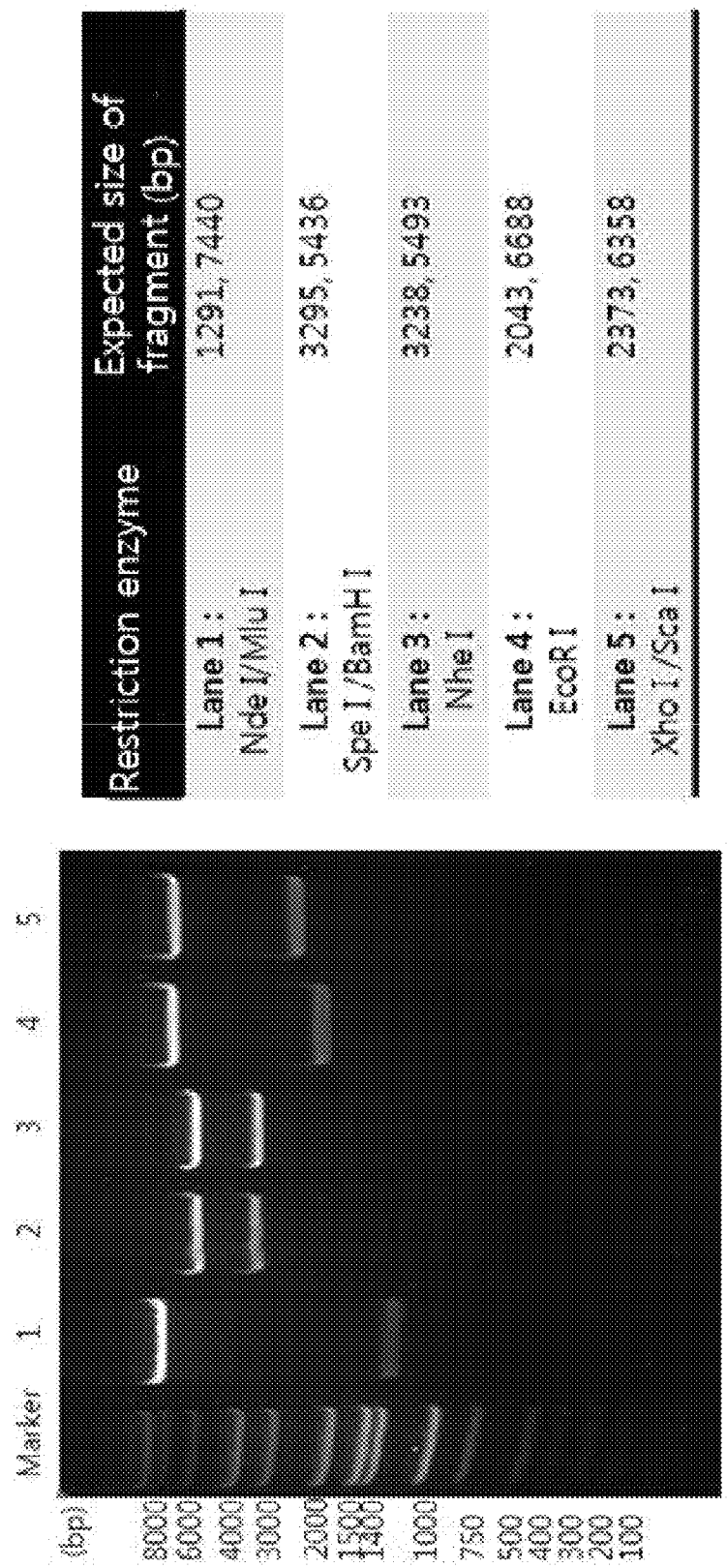
FIG. 5 shows restriction enzyme mapping results for evaluating the structure of the pMIN-E1 retroviral vector.

The DNA fragment obtained after the treatment of the pGemT-E1 vector with the Sca I restriction enzyme was again treated with Mlu I and BamH I restriction enzymes to obtain DNA fragment. The obtained DNA fragment was litigated to the MIN retroviral vector, which was previously treated with MluI and BamHI restriction enzymes, to prepare MIN-E1 retroviral vector. The thus prepared MIN-E1 retroviral vector includes sequences coding adenovirus E1 (nucleotides 560-3509) and Neo$^R$ under the regulation of the MLV LTR promoter. In addition, this vector was evaluated to have a correct structure by restriction enzyme mapping. Further, partial sequences of the obtained structure were verified by PCR analysis. There is no change in the nucleotide sequence (FIGS. 4 and 5).

1-5. Production of MIN-E1 Retrovirus

Retroviruses for E1 gene transfection were produced using plasmid DNA transfection (Soneoka Y et al., 1995). The transfection was conducted by using the Cellphect phosphate calcium transfection system (GE Healthcare BioSciences, NJ, USA) according to the manufacturer's protocol. 293T cell lines seeded at $1\times10^6$ cells one day before transfection were transfected with MIN-E1 retroviral vector, gag-pol expression vector, and env expression vector, and then the cells were cultured for 48 hours. Upon completion of culturing, the cell culture liquid was all harvested, and then filtered through a 0.45-μm filter. The produced MIN-E1 retroviruses were frozen at −80° C. before use.

1-6. Selection of MIN-E1 Retrovirus Envelope

Figure 6:
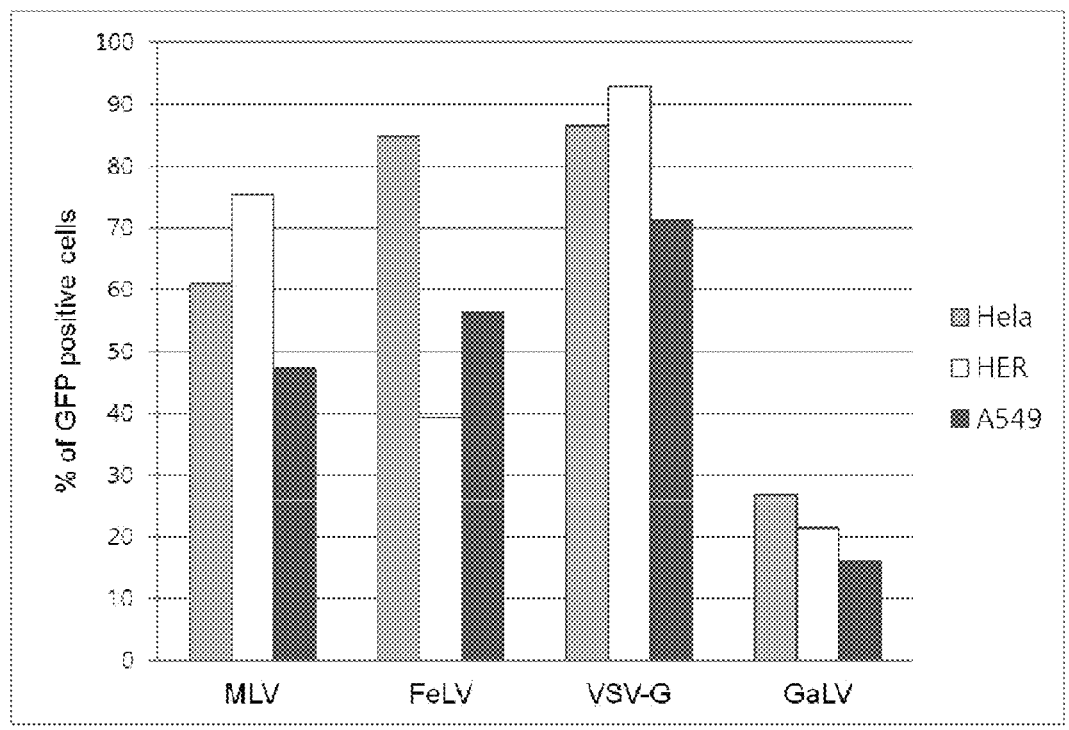
FIG. 6 shows envelope delivery efficiency results when GFP expressing retroviruses having four different envelopes were delivered into three cell lines. The results are used to select the envelope exhibiting the optimum delivery efficiency.
Figure 7:
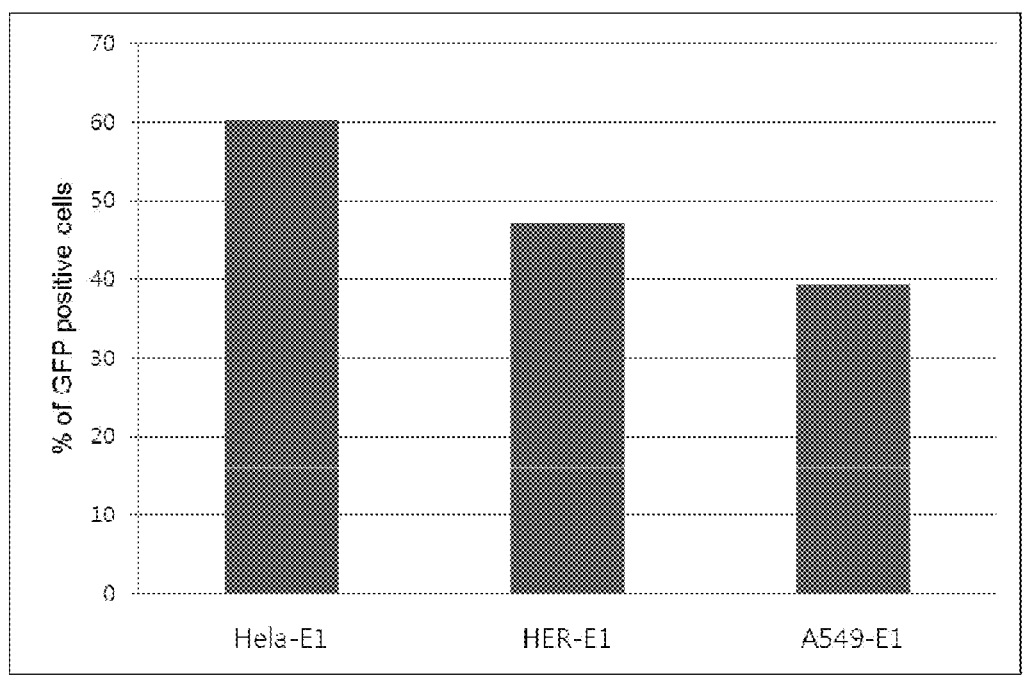
FIG. 7 shows evaluation results of virus production capacity of three cell lines expressing adenovirus E1 gene. GFP expression recombinant adenoviruses produced from the respective cell lines were used to transfect HeLa cells, and the virus content was evaluated by the delivery efficiency.
Figure 8:
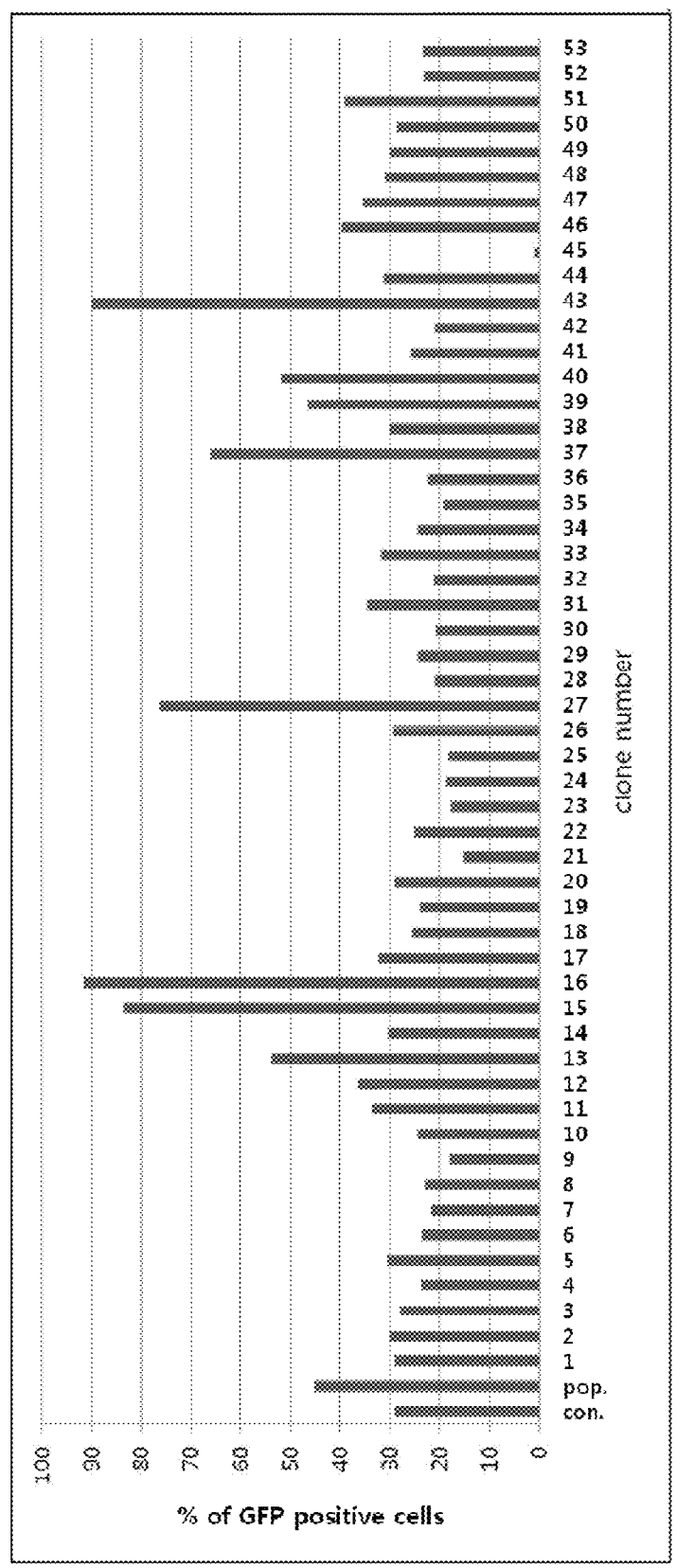
FIG. 8 shows that adenovirus E1 gene expressing HeLa cell clones exhibiting the highest virus production capacity were prepared and the clone exhibiting the most excellent capacity was selected therefrom.

For the efficient induction of transfection into target cells, green fluorescent protein (GFP) retroviruses having four different envelops were produced and compared. The GFP retroviruses having four envelopes of vesicular stomatitis virus glycoprotein (VSV-G) envelope, gibbon ape leukemia virus (GaLV) envelope, feline leukemia virus (FeLV) envelope, and Molony murine leukemia virus (MLV) envelope were produced using the above-described plasmid DNA transfection to induce the transfection into target cell lines at an MOI of 1. Polybrene (8 μg/ml) was added to improve the transfection efficiency. It was verified that the GFP retroviruses having VSV-G envelope exhibited the highest transfection efficiency in all three target cell lines (FIG. 6).

Example 2

Preparation of Adenovirus E1 Gene-Expressing Adenovirus Producing Cell Line 2-1. Cell Line and Cell Culture Cell lines used in the present invention were a total of three: A549 human bronchogenic carcinoma cell line (CCL-185; ATCC, MD, USA), human embryonic retinoblast (CRL-2302; ATCC, MD, USA), and human HeLa cervical carcinoma cell line (CCL-2; ATCC, MD, USA). These cells were cultured in Dulbecco's Modified Eagle's medium (DMEM) supplemented with 10% fetal bovine serum and antibiotics at 37° C. under 5% $CO_2$. The cell culture medium, reagent, and serum were purchased from Gibco (Gibco BRL life technologies, inc., MD, USA), and plastic products for culture were purchased from BD Falcon (BD Falcon, N.J., USA).

2-2. Selection of Adenovirus Producing Cell Lines Through Comparison of Recombinant Adenovirus Production Capacity Among Cell Lines For the selection of a cell line exhibiting the highest capacity in recombinant adenovirus production among three candidate cell lines, adenovirus E1 gene-expressing cell lines from the three cell lines were produced. The cells were respectively seeded in the 6-well plate at $1\times10^6$ per well one day before transfection with MIN-E1 retrovirus. On the day of transfection, the retroviruses were added at an MOI of 1.5, and polybrene (8 μg/ml) was added to improve the transfection efficiency. The cells were cultured for 24 hours, followed by treatment with trypsin, and then the cells were all collected. The collected cells were again seeded on the 100-mm culture dish, followed by addition of G418 (1 mg/ml), and then the cells were cultured for 14 days, thereby obtaining G418-resistant cell lines. For the comparison of recombinant adenovirus production capacity among the thus obtained three adenovirus E1-expressing cell lines, the cells were transfected with E1-deficient adenoviral vector (nucleotides 560-3328, U.S. Pat. No. 5,731,172) and adenovirus production capacity thereof was evaluated. The G418-resistant cells were seeded in the 24-well plate at $1\times10^6$ per well one day before the transfection, and transfected with GFP-expressing adenoviral vector at an MOI of 100 on the day of the transfection. After culturing for three days, all the cells were treated with trypsin, and then harvested. The harvested cells were sonicated and centrifuged, and then only the supernatant was taken. For the evaluation of the adenovirus content in the supernatant, 5 μl of the supernatant obtained from each cell line was added to HeLa cells seeded in the 24-well plate at $0.6\times10^5$ per well one day before. After culturing for two days, GFP expression was confirmed by flow cytometry. It was verified that the adenovirus E1-expressing cell line prepared from the HeLa cell line had the highest virus content, and thus had the highest recombinant adenovirus production capacity.

2-3. Production of Adenovirus E1 Gene-Expressing HeLa Cell Line Clones

HeLa cells were seeded in the 6-well plate at $1\times10^5$ per well one day before transfection with MIN-E1 retrovirus. On the day of transfection, the retroviruses were added at an MOI of 1.5, and polybrene (8 μg/ml) was added to improve the transfection efficiency. The cells were cultured for 48 hours, followed by treatment with trypsin, and then the cells were all collected. The collected cells were again seeded on a 100-mm culture dish, followed by addition of G418 (1 mg/mg), and then cultured until colonies are formed. If one cell colony grows to have a diameter of approximately 5 mm, clones were selected using a cloning cylinder (Millipore, Mass., USA). As a result, 53 G418-resistant clones were obtained. The selected 53 clones were cultured in a 96-well plate, and when clone growth was completed, the clones were expansively cultured into a 24-well plate and a 6-well plate. When clone growth was completed in the 6-well plate, the clones were cultured in a 100-mm culture dish, thereby preparing cell stocks.

2-4. Selection of Clones Having Excellent Recombinant Adenovirus Production Capacity For the selection of a clone exhibiting the highest virus production capacity among cell clones, 53 frozen cell clone stocks were all thawed, and then cultured for 3 days. The cells of the thawed clones were seeded in a 24-well plate at $1\times10^5$ per well one day before transfection, and transfected with GFP-expressing adenoviral vector at an MOI of 100 on the day of the transfection. After culturing for three days, all the cells were treated with trypsin, and then harvested. The harvested cells were sonicated and centrifuged, and then only the supernatant was taken. For the evaluation of the adenovirus content in the supernatant, 5 μl of the supernatant obtained from each cell clone was added to HeLa cells seeded in a 24-well plate at $0.6\times10^5$ per well one day before. After culturing for two days, GFP expression was confirmed by flow cytometry. It was verified that Clone 16 had the highest virus content and thus had the highest recombinant adenovirus production capacity, and this clone was named H2C16 (FIG. 18).

Example 3

Characterization of H2C16 Clone 3-1. PCR Analysis of H2C16 Clone

Figure 9B:
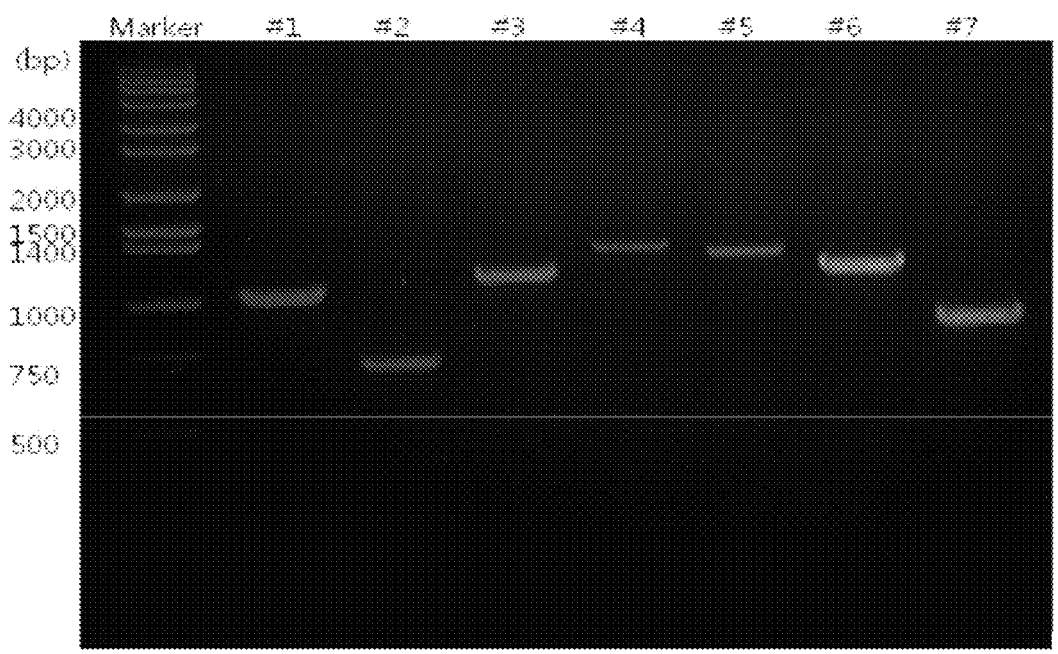
FIG. 9b shows PCR analysis results for evaluating the structure of the retrovirus inserted into the chromosome of the clone (No. 16, called H2C16) selected from the results.

When the gene is delivered using the retroviral vector, the retroviral vector including the gene is inserted in the cellular genome DNA. For the confirmation whether the retroviral vector used to produce the H2C16 clone and the Ad-E1 gene were inserted into the cellular genome DNA in a correct structure, MIN-E1 retroviral vector-specific primers of SEQ ID NO: 7-12 (MIN-E1 #1 to 7 primers, Table 1) were designed to amplify DNA bands by the PCR method, and structures thereof were evaluated through sequencing. First, the genome DNA was extracted from the H2C16 clone using a genome DNA extraction kit (Qiagen, Calif., USA). After that, PCR reaction was induced by using the extracted genome DNA as a template and combining respective specific primer sets. It was confirmed that the sizes of the bands amplified on the gel were identical to the expected band sizes through comparison and the MIN-E1 retroviral vector was inserted into the genome DNA of H2C16 in a correct structure (FIG. 9).

3-2. Linear Amplification Mediated-Polymerase Chain Reaction (LAM-PCR) Analysis of H2C16 Clone For the verification of the site of the delivered MIN-E1 retroviral vector inserted into the H2C16 clone genome DNA and the copy number thereof, LAM-PCR was conducted. First, the genome DNA was extracted from the H2C16 clone using a genome DNA extraction kit (Qiagen, Calif., USA). PCR was performed using 10 ng of the extracted genome DNA as a template and a primer of SEQ ID NO: 21 (LTR primer, Table 1). The PCR was run under the conditions of 50 cycles of 1 minute at 95° C., 45 seconds at 72° C., and 90 seconds at 72° C., and then Taq polymerase was added and the PCR was run for another 50 cycles under the same conditions a (①a linear amplification procedure). After the PCR reaction, Dynabeads® M-280 streptavidin (DNA kilobase binder kit: Dynal, Oslo, Norway) and binding solution (DNA kilobase binder kit: Dynal, Oslo, Norway) were added to the product, followed by reaction at room temperature for 12 hours or longer, thereby inducing the formation of DNA-bead complex. The DNA-bead complex was isolated using a magnetic particle concentrator (DYNAL MPC-9600: Invitrogen, CA, USA) (②a magnetic capture procedure). A hexanucleotide mixture (Roche Applied science, IN, USA), dioxyribonucleotide (dNTP), and Klenow polymerase were added to the DNA-bead complex, followed by reaction at 37° C. for 1 hour, thereby inducing the synthesis of double-stranded DNA (③ a hexanucleotide-priming procedure). After that, the Tsp509I restriction enzyme was added to the synthesized reactant, followed by reaction at 37° C. for 1 hour (④ a Tsp509I cleavage procedure). A linker cassette, a ligation buffer, adenosine triphosphate (ATP), and Fast-Link® DNA ligase (Fast-link DNA ligase kit: Epicentre Biotechnologies, WI, USA) were added, followed by reaction at room temperature for 5 minutes, thereby ligating a linker to the cleaved region (⑤ a linker ligation procedure). 0.1 N NaOH was added, followed by reaction at room temperature for 10 minutes, thereby isolating DNA from the DNA-bead complex (⑥ a denature procedure). The first PCR was run using 2 µl of the isolated DNA as a template and primers of SEQ ID NO: 22 (LC I primer, Table 1) and SEQ ID NO: 23 (LTR II primer, Table 1). The PCR reaction was run under the conditions of 30 cycles of 1 minute at 65° C., 45 seconds at 72° C., and 90 seconds at 72° C.

After that, the second PCR was run using 1 µl of the first PCR product as a template and primers of SEQ ID NO: 24 (LC II primer, Table 1) and SEQ ID NO: 25 (LTR III primer, Table 1). The PCR reaction condition were the same as those of the first PCR (⑦ an exponential PCR procedure).

Figure 10A:
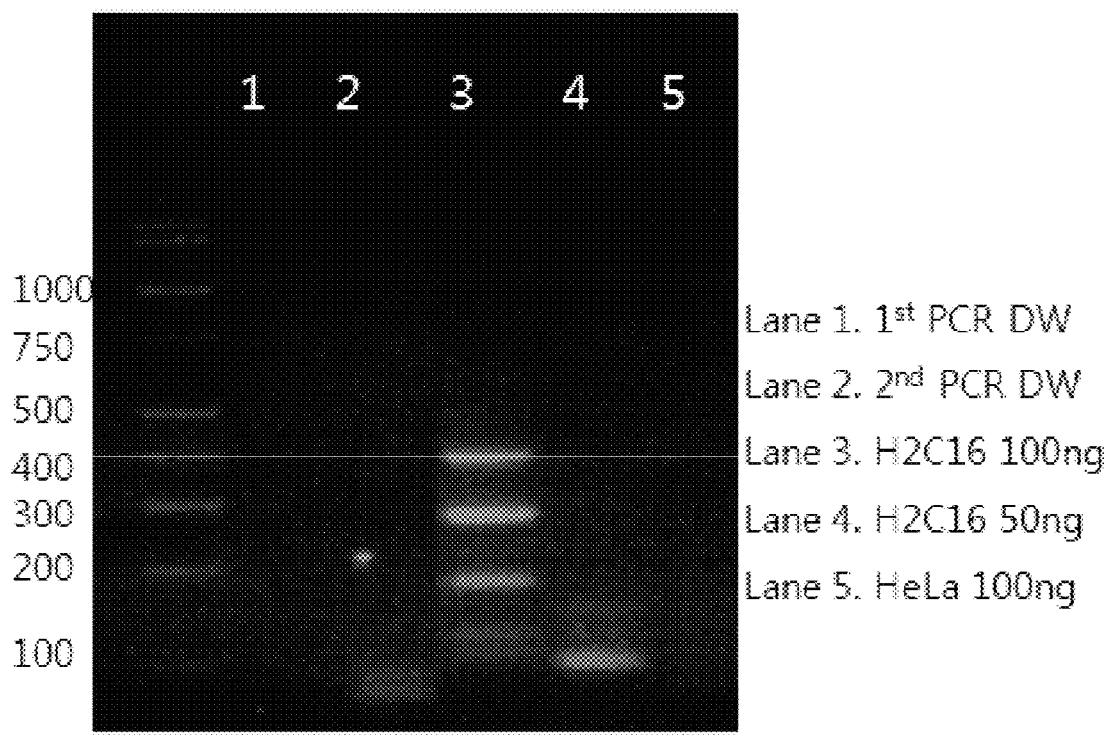
FIG. 10a shows linear amplification mediated-polymerase chain reaction (LAM-PCR) results for analyzing the site of the retroviral vector inserted into the chromosome of H2C16. Lanes 1 and 2 show negative reaction results, and Lanes 3 and 4 show results according to concentrations of H2C16 clone. Blast data were results obtained by isolating and sequencing all bands shown on Lanes 3 and 4.
Figure 10B:
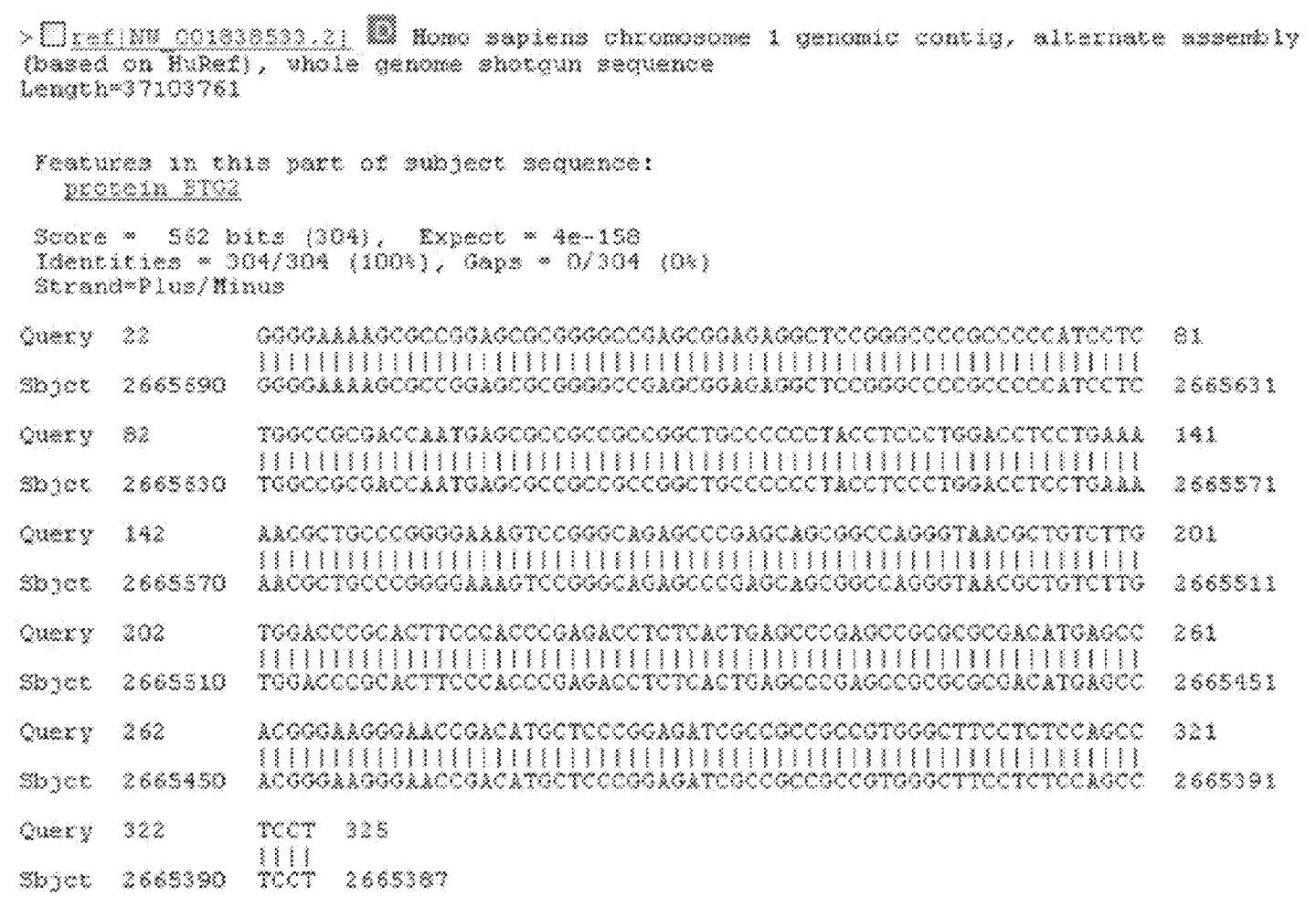

After the second PCR, the bands were confirmed on the 2.5% agarose gel, isolated using the Qiagen II gel extraction kit (Qiagen, Calif., USA), and then cloned into the pGem-T Easy vector system (Promega, Wis., USA), followed by sequencing. As a result of sequencing of all the bands for the H2C16 clone, it was confirmed that the sequences of all the bands were identical, and located at the B-cell translocation gene 2 (BTG2) site of Chromosome 1. These results confirmed that only one copy of the MIN-E1 retroviral vector, which was delivered for E1 gene introduction, was inserted into Chromosome 1 of the H2C16 clone (FIG. 10).

3-3. Analysis of E1 Expression of H2C16 Clone

E1A, E1B19K, and E1B55K expressions were confirmed from the H2C16 clone. E1A expression was confirmed through protein expression by western blotting, and E1B19K and E1B55K expressions were confirmed through RNA expression by RT-PCR. First, for the confirmation of E1A protein expression, H2C16 clones and HeLa cells of $1 \times 10^6$ for each were treated with trypsin and then harvested, followed by centrifugal washing with PBS. 100 µl of a reporter lysis buffer (Promega, Wis., USA) was added, and then the cells were allowed to stand at room temperature for 5 minutes. After that, the reaction at −70° C. for 5 minutes and the reaction at 37° C. for 5 minutes were repeated three times. After centrifugation, the protein concentration in the supernatant was quantified by the Bradford (Bio-rad, CA, USA) method. 50 µg of protein was loaded on 4-12% Bis-Tris gel (Invitrogen, CA, USA), followed by electrophoresis at 120 V for 90 minutes, and then a membrane (GE Healthcare Bio-Sciences, NJ, USA) was placed on the gel, followed by again electrophoresis at 12 V for 20 minutes. The membrane washed once with TBS (20 mM Tris-Hcl, 137 mM Nacl, pH 7.6) solution was placed in the blocking solution (TBST; 5% skim milk dissolved in TBS+0.5% tween 20), and then, 10 µg of primary antibody (mouse anti-adenovirus type 5 E1A, BD BioSciences, CA, USA) was added, followed by reaction at 4° C. for one day. The membrane was washed three times with TBST and then placed in the blocking solution, and then secondary antibody (goat anti-mouse IgG-HRP, Thermo Fisher scientific, IL, USA) diluted to 1/2000 was added, followed by reaction at room temperature for 2 hours. The membrane was again washed with TBST, and a developing solution (Santacruz, Calif., USA) was applied thereto, thereby confirming bands.

Figure 11:
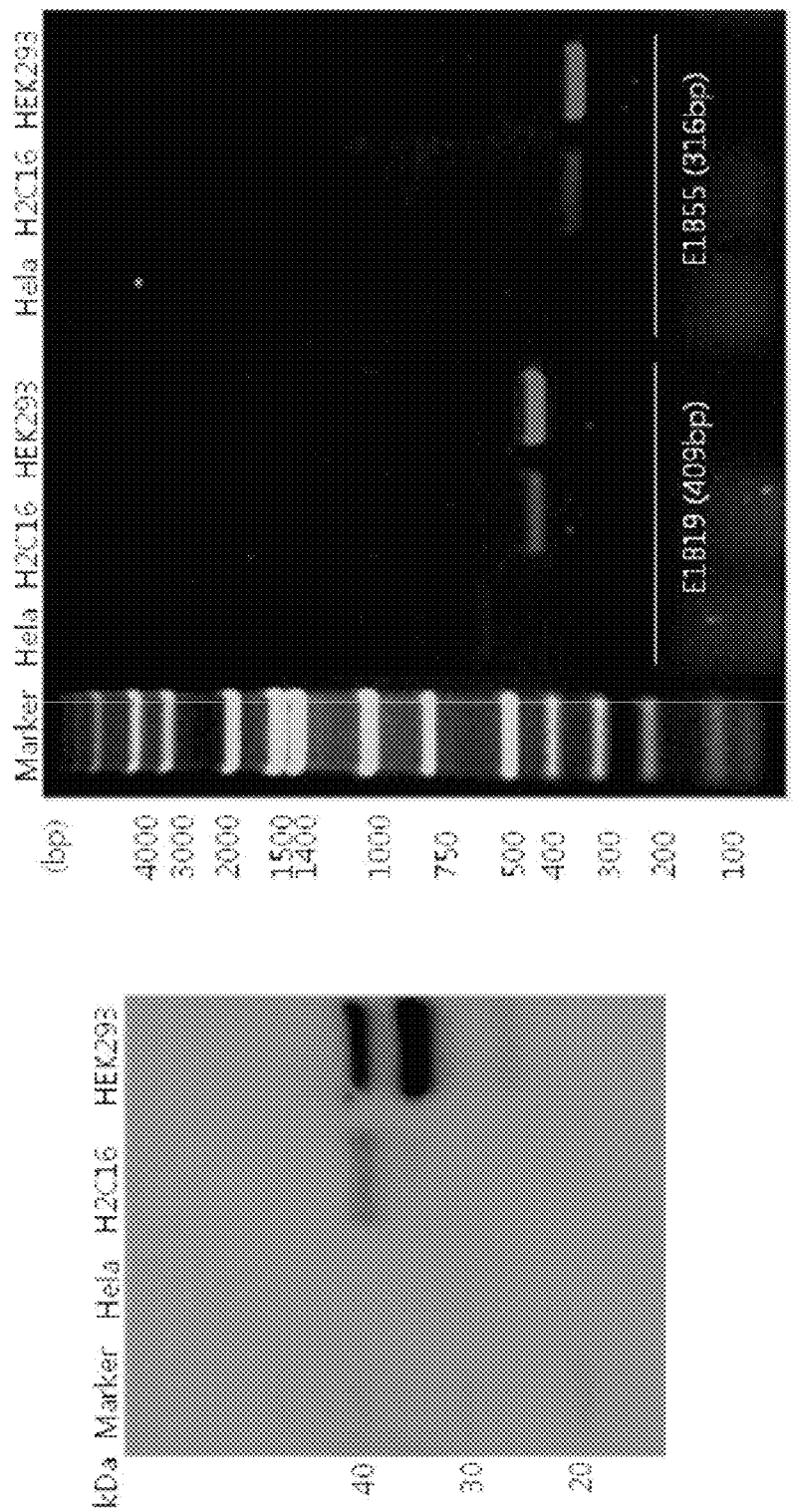
FIG. 11 shows E1A, E1B19K, and E1B55K expressions confirmed from H2C16 clones. Protein expression for E1A was confirmed by western blotting, and RNA expressions for E1B19K and E1B55K were confirmed by PCR.

For the confirmation of E1B19K and E1B55K RNA expressions, H2C16 clones and HeLa cells of $1 \times 10^6$ for each were treated with trypsin and then harvested, followed by centrifugal washing with PBS. The cells were treated with Triazole (Invitrogen, CA, USA), and RNA was extracted from the cells. The extracted RNA was used as a template to synthesize cDNA. For the confirmation of E1B19K RNA expression, PCR was run using primers of SEQ ID NO: 26 (B19-F primer, Table 1) and SEQ ID NO: 27 (B19-R primer, Table 1), and for the confirmation of E1B55K RNA expression, PCR was run using primers of SEQ ID NO: 28 (B55-F primer, Table 1) and SEQ ID NO: 29 (B55-R primer, Table 1). After that, E1B19K and E1B55K RNA expressions were confirmed by confirming the presence or absence of PCR amplification products and sizes thereof (FIG. 11).

Figure 12:
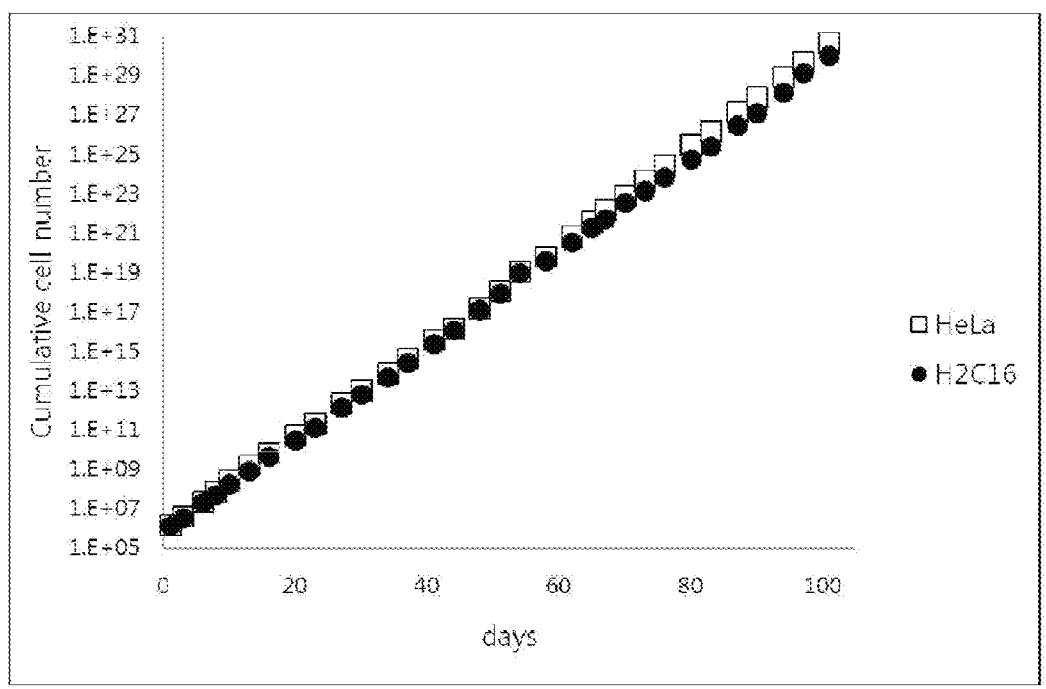
FIG. 12 shows comparison results of cell growth rate while H2C16 clones and their mother cells, HeLa cells, were serially cultured for 101 days. There was no large difference in cell growth therebetween.

3-4. Cell Growth Rate Curve of H2C16 Clone H2C16 clones and parent cells, H2La cells, were serially cultured for 101 days, and cell growth rates thereof were compared. As a result, it was verified that the H2C16 clones and H2La cells are well grown without a large difference in growth therebetween (FIG. 12).

Example 4

Comparison of Recombinant Adenovirus

Production Capacity Between H2C16 Clones and HEK293 Cells 4-1. Verification on Recombinant Adenovirus Production Capacity on a Small Scale For the verification of recombinant adenovirus production capacity of H2C16 clones, recombinant adenoviruses were produced using T-25 cm2 flask (IWAKI, Chiba, Japan) on a small scale. Here, also for the verification of recombinant adenovirus production capacity of HEK293 cells, the same method was used to produce recombinant adenoviruses. First, for the verification of recombinant adenovirus production capacity on a small scale, $2.5 \times 10^6$ HEK293 cells and $1 \times 10^6$ H2C16 clones were seeded in the T-25 cm² flask one day before transfection. On the day of transfection, the media were all removed, and then adenovirus (Ad)-GFP recombinant adenoviruses were added at MOI of 2, 10, and 20 in media containing 500 μl of 5% fetal bovine serum in respective flasks, and then transfection was induced by shaking the flasks at intervals of 20 minutes for 1 hour. After that, 4.5 ml of a medium containing 5% fetal bovine serum was added, followed by culturing for three days. After the three days, all the cells were collected, and then the procedure of quickly freezing the cells in liquid nitrogen and completely thawing the cells at 37° C. was repeated three times. The cells were centrifuged at 12000 rpm for 5 minutes at 4° C., and then the supernatants were harvested and stored at −80° C.

Figure 13:
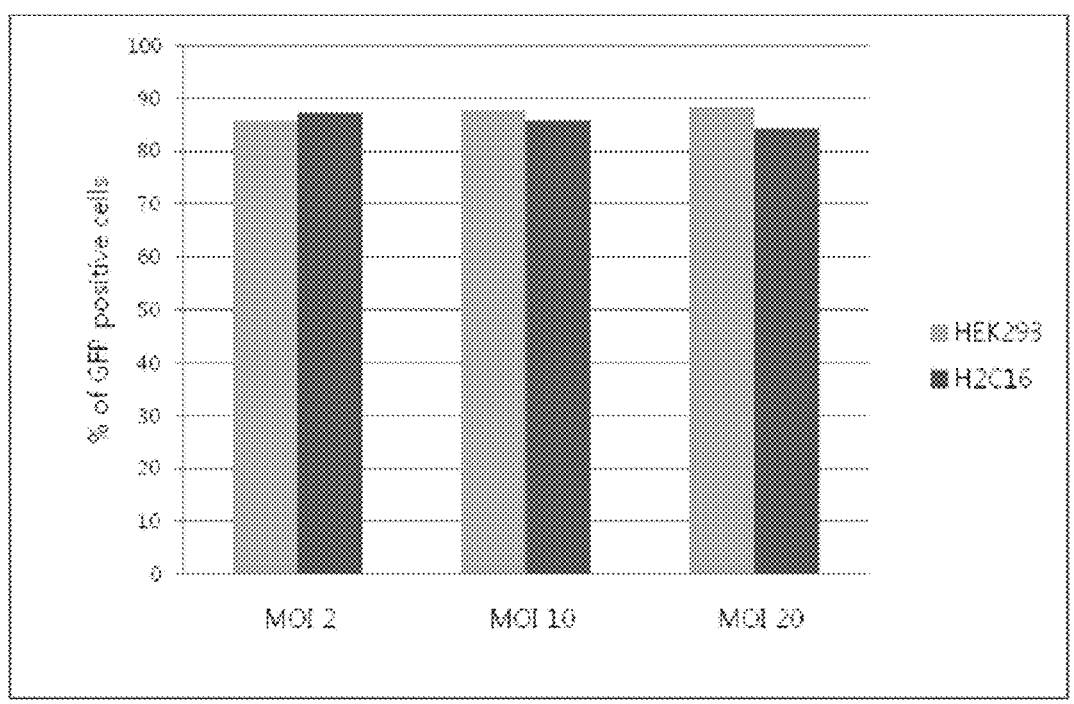
FIG. 13 shows comparison results of recombinant adenovirus production capacity between H2C16 clones and HEK293 cells. Viruses were produced on a small scale under a total of three infection conditions and the production capacity was compared between the two cell lines.

For the evaluation of adenovirus content in the harvested supernatant, 5 μl of the supernatants harvested from the HEK293 cells and H2C16 clones were added to the HeLa cells seeded at $0.6 \times 10^5$ per well in a 24-well plate one day before, and then the cells were cultured for two days. After that, the recombinant adenovirus content was verified by defining the percentage of GFP-expressing cells using the flow cytometry. As a result, excellent production capacity of H2C16 clones was confirmed in all the three MOI conditions, and the levels thereof were similar to that of viruses produced from HEK293 cells. However, since the cell number of H2C16 seeded was 2.5 times less than that of HEK293, the yield of viruses per cell by H2C16 may be about 2.5 times higher than that by HEK293 (FIG. 13).

Figure 14:
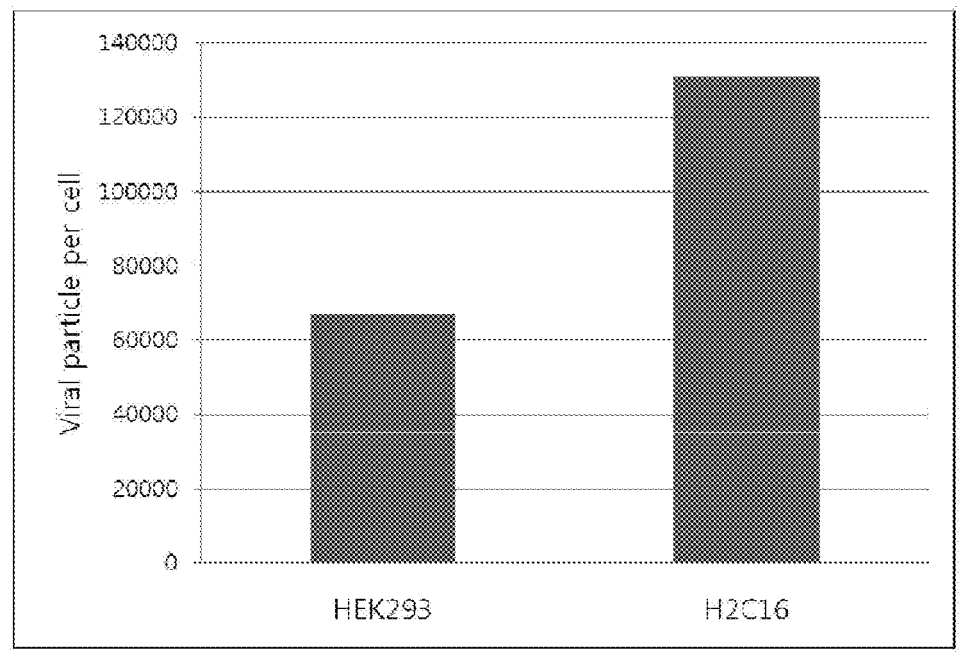
FIG. 14 shows comparison results of production capacity between the two cell lines. Viruses were produced on a larger scale than the above production conditions, followed by virus purification, and then viruses produced from the two cell lines were quantified.

4-2. Verification on Recombinant Adenovirus Production Capacity on a Large Scale For the verification of recombinant adenovirus production capacity of H2C16 clones on a large scale, $2.25 \times 10^7$ HEK293 cells and $0.9 \times 10^7$ H2C16 clones were seeded in the T-225 cm² flasks one day before transfection. On the day of transfection, the media were exchanged with media containing 5% fetal bovine serum, and then Ad-GFP recombinant adenoviruses were added at an MOI of 15 in the respective flasks, followed by culturing for three days. After the three days, all the cells were collected, and then the procedure of quickly freezing the cells in liquid nitrogen and completely thawing the cells at 37° C. was repeated three times. The cells were centrifuged at 12000 rpm for 5 minutes at 4° C., and then the supernatants were harvested and stored at −80° C. For the measurement of accurate recombinant virus titer, viruses were purified using cesium chloride. Recombinant adenoviral particles were measured using the UV measuring method, and the yield of recombinant adenoviruses was estimated through the measurement results. As a result, the amount of recombinant adenoviruses production was $1.51 \times 10^{12}$ viral particles/ml for HEK293 cells and $1.18 \times 10^{12}$ viral particles/ml for H2C16 clones. In terms of the yield per cell, the production capacity of H2C16 was 1.95 times higher than that of HEK293 (FIG. 14). The level of infecting viral particles was analyzed by 50% tissue culture infection dose (TCID50) assay. The results confirmed that both of two viruses had equivalent virus quality.

Example 5

Figure 15:
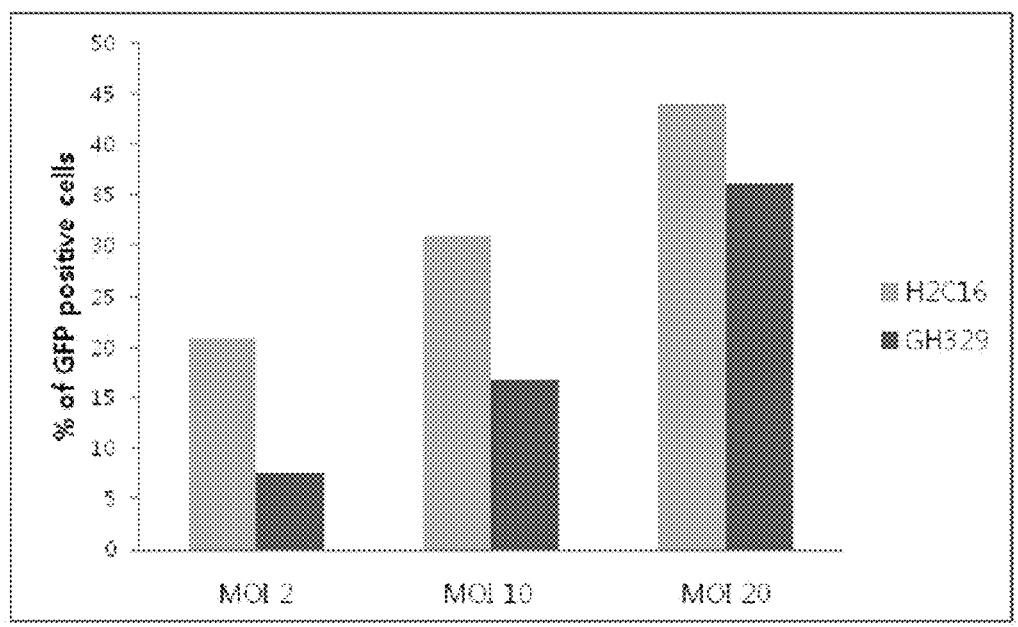
FIG. 15 shows comparison results in recombinant adenovirus production capacity between H2C16 clones and GH329 cells. Viruses were produced on a small scale under a total of three infection conditions and the production capacity was compared between the two cell lines.

Comparison of Recombinant Adenovirus Production Capacity Between H2C16 Clones and GH329 Cells GH329 cells developed based HeLa cells include a region of nucleotides 511-3924 of the wild-type adenovirus type 5 DNA, and are an adenovirus producing cell line into which the plasmid regulated by phosphoglycerate kinase (PGK) promoter is transduced. For the comparison of adenovirus production capacity between H2C16 clones and GH329 cells, recombinant adenoviruses were produced using T-25 cm² flasks (IWAKI) on a small scale. H2C16 clones and GH329 cells were seeded at $1 \times 10^6$ for each in T-25 cm² flasks one day before infection. On the day of infection, the media were all removed, and then Ad-GFP recombinant adenoviruses were added at MOI of 0.5, 1, and 5 in media containing 500 μl of 5% fetal bovine serum in the flasks, and then infection was induced by shaking the flasks at intervals of 5 minutes for 1 hour. After that, 4.5 ml of media containing 5% fetal bovine serum were added thereto, followed by culturing for three days. After the three days, all the cells were collected, and then the procedure of quickly freezing the cells in liquid nitrogen and completely thawing the cells at 37° C. was repeated three times. The cells were centrifuged at 12000 rpm for 10 minutes at 4° C., and then the supernatants were harvested and stored at −80° C. For the evaluation of adenovirus content in the harvested supernatant, 1 μl of the supernatants harvested from the H2C16 clones and GH329 cells were added to the HeLa cells that were seeded at $0.6 \times 10^5$ per well in a 24-well plate one day before, and then the cells were cultured for two days. After that, the recombinant adenovirus content was verified by defining the percentage of GFP expressing cells using the flow cytometry. As a result, it was verified that the production capacity of H2C16 cells as compared with GH329 cells was excellent in all the three MOI conditions, and especially, the production capacity of H2C16 cells was 2.7 times higher than that of GH392 cells in the lowest MOI of 0.5 (FIG. 15).

Example 6

Confirmation of Replication-Competent Adenovirus (RCA) Production of H2C16 Clone 6-1. Confirmation of RCA Production Using Unpurified Adenoviruses The possibility of RCA production was evaluated when replication-incompetent adenoviruses were produced in H2C16 clones. One day before infection, $4.5 \times 10^6$ H2C16 clones were seeded in T-75 cm² flask (Falcon) and $9 \times 10^6$ HEK293 cells as a control group were seeded in T-75 cm² flask (Corning). On the day of infection, the media were all removed, and then replication-incompetent adenoviruses were added at an MOI of 10 in media containing 5% fetal bovine serum in the flasks, followed by reaction for three days. After three days, all the cells were collected. The cells were sonicated while a sonicator repeated the 30 sec work/1 min rest cycle for 10 minutes, and then centrifuged at 12000 rpm for 10 minutes at 4° C. The supernatants were harvested and then stored at −80° C. Meanwhile, H2C16 clones and HEK293 cells were seeded in T75 cm² flasks as in the above, and the frozen supernatants harvested from respective cells were thawed to infect the cells. The adenovirus producing procedure was repeated until RCA was confirmed. The presence or absence of RCA in the recombinant adenoviruses in the harvested supernatants was evaluated by PCR. 5 μl of the supernatants harvested from H2C16 clones and HEK293 cells were added to HeLa cells that were seeded in a 24-well plate at $3 \times 10^5$ per well one day before, followed by culturing for two days. After that, the genomic DNA was isolated from the HeLa cells, and the presence or absence of amplification products was confirmed by PCR using primers of SEQ ID NO: 30 (RCA-F primer, Table 1) and SEQ ID NO: 31

Figure 16A:
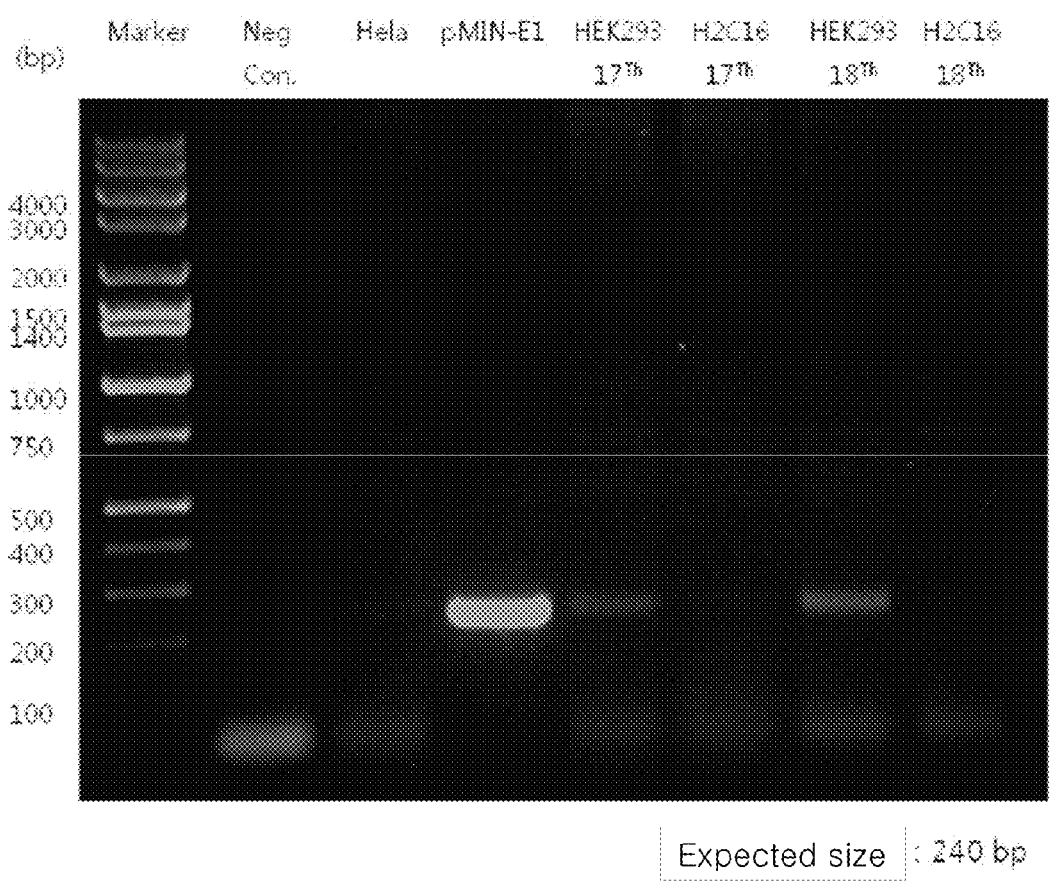
FIG. 16a shows evaluation results of the possibility of RCA production when replication-incompetent adenoviruses were produced from H2C16 clones. H2C16 clones were subjected to continuous virus production and amplification together with HEK293 cells. H2C16 clones exhibited the lower possibility of RCA production than HEK293 cells. The negative control group (Neg Con.) and the HeLa lane show negative results and the pMIN-E1 lane shows a positive result. HEK293 $17^{th}$, HEK293 $18^{th}$, H2C16 $17^{th}$, H2C16 $18^{th}$ lanes show results from $17^{th}$ and $18^{th}$ adenoviruses harvested from the respective cells.

(RCA-R primer, Table 1) that amplify nucleotides 560-800, corresponding to an internal region of the E1 gene of adenovirus type 5 DNA. As a result, RCA was not confirmed in viruses that were repeatedly produced several times from H2C16 clones, but RCA was confirmed in viruses that were repeatedly produced several times from HEK293 cells (FIG. 16a).

6-2. Confirmation of RCA Production Using Purified Adenoviruses

Figure 16B:
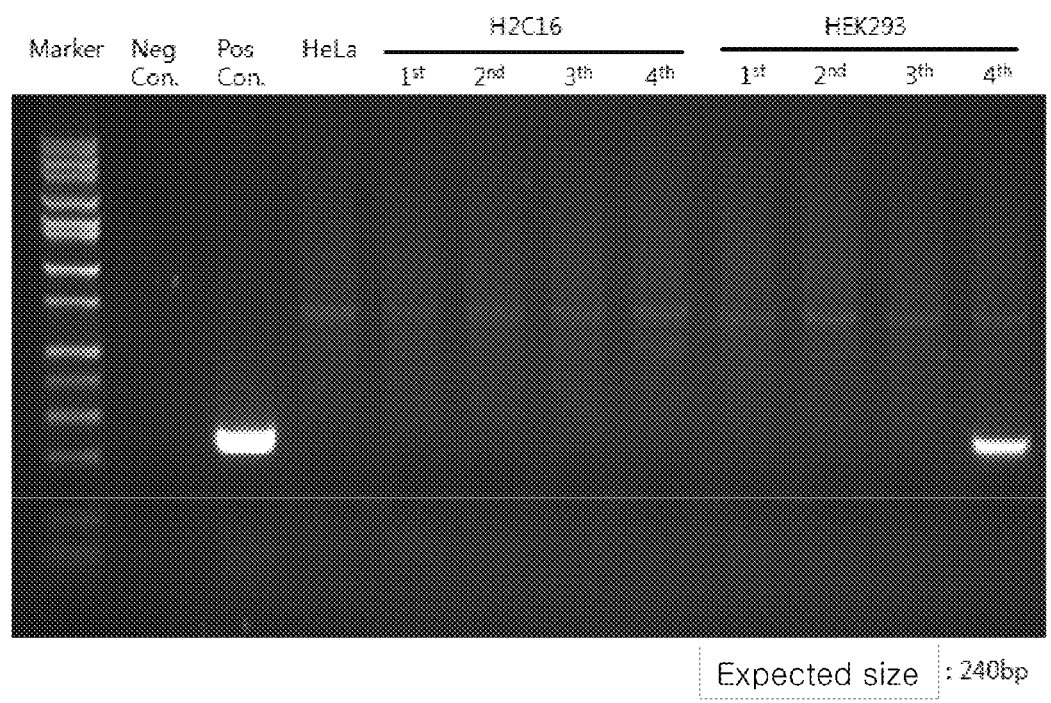
FIG. 16b shows evaluation results of the possibility of RCA production when replication-incompetent adenoviruses were produced from H2C16 clones. H2C16 clones were subjected to continuous virus production, amplification, and purification together with HEK293 cells. H2C16 clones exhibited the lower possibility of RCA production than HEK293 cells. The negative control group (Neg Con.) and the HeLa lane show negative results, and the positive control group (Pos Con.) shows a positive result. H2C16 $1^{st}$, $2^{nd}$, $3^{rd}$, and $4^{th}$ and HEK293 $1^{st}$, $2^{nd}$, $3^{rd}$, and $4^{th}$ lanes show results from $1^{st}$, $2^{nd}$, $3^{rd}$, and $4^{th}$ adenoviruses harvested and purified from the respective cells.

The possibility of RCA production was evaluated when replication-incompetent adenoviruses were produced in H2C16 clones. One day before infection, $1.35 \times 10^7$ H2C16 clones were seeded in T-225 cm² flask (Falcon) and $2.7 \times 10^7$ HEK293 cells as a control group were seeded in T-225 cm² flask (Corning). On the day of infection, the media were all removed, and then replication-incompetent adenoviruses were added at an MOI of 20 in media containing 5% fetal bovine serum in the flasks, followed by reaction for three days. After three days, all the cells were collected. The cells were sonicated while a sonicator repeated the 30 sec work/1 min rest cycle for 10 minutes, and then centrifuged at 12000 rpm for 10 minutes at 4° C. The supernatants were harvested and then stored at −80° C. Meanwhile, H2C16 clones and HEK293 cells were seeded in T-225 cm² flasks as in the above, and the frozen supernatants harvested from respective cells were thawed to infect the cells. The remainder supernatants were purified using cesium chloride (CsCl), and then concentrated. The adenovirus producing procedure was repeated until RCA was confirmed. The presence or absence of RCA in the purified recombinant adenoviruses was evaluated by PCR. 1000 viral particles/cell of the purified viruses harvested from H2C16 clones and HEK293 cells were added to HeLa cells that were seeded at $1 \times 10^6$ in T-25 cm² flasks (Iwaki) one day before, followed by culturing for 14 days. After that, the genomic DNA was isolated from the HeLa cells, and the presence or absence of amplification products was confirmed by PCR using primers of SEQ ID NO: 30 (RCA-F primer, Table 1) and SEQ ID NO: 31 (RCA-R primer, Table 1) that amplify nucleotides 560-800, corresponding to an internal region of the E1 gene of adenovirus type 5 DNA. As a result, RCA was not confirmed in viruses that were repeatedly produced several times from H2C16 clones, but RCA was confirmed in viruses that were repeatedly produced several times from HEK293 cells (FIG. 16b).

Example 7

Comparison of Target Protein (3E8 Antibody) Production Capacity Between H2C16 Clones and HeLa Cells 7-1. Preparation of pMT-Heavy Chain and pMT-Light Chain Retroviruses For the comparison of target protein production capacity between H2C16 clones and parent cells, H2La cells, 3E8 antibodies were used. Prior to the production capacity comparison test, 3E8 antibody-expressing retroviruses were prepared. 3E8 antibodies are humanized anti-TAG-72 antibodies, and disclosed in US Patent Publication No. US2008/0279847. Heavy chain and light chain sequences of the 3E8 antibody were amplified from pdCMV-dhfr-3E8 vector by PCR using primers of Table 2 below. Here, since each of primers bound to 5'-regions of the heavy chain and light chain of the pdCMV-dhfr-3E8 vector includes a sequence of BamH I restriction enzyme, and each of primers bound to 3'-regions thereof includes a sequence of Xho restriction enzyme, the amplified PCR product has a sequence of BamH I—heavy chain—Xho I or BamH I—light chain—Xho I. The obtained DNA structures were ligated to MT retroviral vectors that were previously treated with BamH I and Xho I restriction enzymes, to prepare MT-heavy chain and MT-light chain retroviral vectors.

Retroviruses for transfection of heavy chain and light chain genes were produced using plasmid DNA transfection (Soneoka Y et al., 1995). The transfection was conducted by using the Cellphect phosphate calcium transfection system (GE Healthcare BioSciences, NJ, USA) according to the manufacture's protocol. 293T cell lines seeded at $1 \times 10^6$ cells one day before were transfected with MT-heavy chain or MT-light chain retroviral vector, gag-pol expression vector, and env expression vector, and then the cells were incubated for 48 hours. Upon the completion of incubation, the cell culture liquid was all harvested, and then filtered through a 0.45-μm filter. The produced MT-heavy chain or MT-light chain retroviruses were frozen at −80° C. for use.

TABLE 2

Sequence information of used primers

| SEQ ID NO. | Primer name | Sequence |
|---|---|---|
| 34 | Heavy chain (F) | CGGGATCCATGGAATGGAGCTGGGTC |
| 35 | Heavy chain (R) | CCGCTCGAGTCATTTACCCGGGGACAG |
| 36 | Light chain (F) | CGGGATCCATGGAGACACATTCTCAG |
| 37 | Light chain (R) | CCGCTCGAGTTAACACTCTCCCCTGTTG |

7-2. Comparison of 3E8 Antibody Production Capacity Between H2C16 Clones and HeLa Cells For the verification of 3E8 antibody production capacity of H2C16 clones, the cells were transfected three times with MT-heavy chain retroviruses and two times with MT-light chain retroviruses. Here, HeLa cells were transfected by the same method. One day before transfection with MT-heavy chain retroviruses, H2C16 clones were seeded at $1 \times 10^5$ per well in 6-well plate. On the day of transfection, the retroviruses were added at an MOI of 5, and polybrene (8 μg/ml) was added to improve the transfection efficiency, followed by centrifugation at 2800 rpm for 90 minutes at 32° C. After the centrifugation, the cells were cultured for 2 hours under conditions of 37° C. and 5% $CO_2$, followed by supernatant removal and then new medium replacement. After the cells were cultured for one day, a second transfection was performed by the same method as before. After new medium replacement, the cells were cultured for 6 hours under conditions of 37° C. and 5% $CO_2$, and then all treated with trypsin, followed by cell harvesting. The harvested cells were seeded at $1 \times 10^5$ per well in a new 6-well plate. After the cells were cultured for one day, a third transfection was performed by the same method as before. After new medium replacement, the cells were cultured under conditions of 37° C. and 5% $CO_2$. After the cells were cultured for two days, all the cells were treated with trypsin, followed by cell harvesting, and then the harvested cells were seeded at $1 \times 10^5$ per well in a new 6-well plate. The cells were cultured for two days under conditions of 37° C. and 5% $CO_2$. Then, for the transfection with MT-light chain retroviruses, all the cells were treated with trypsin and harvested, and then seeded at $1 \times 10^5$ per well in a new 6-well plate. The cells were cultured for one day under conditions of 37° C. and 5% $CO_2$. After that, MT-light chain retroviruses were added at an MOI of 5, and then polybrene (8 µg/ml) was added to improve the transfection efficiency, followed by centrifugation at 2800 rpm for 90 minutes at 32° C. After the centrifugation, the cells were cultured for 2 hours under conditions of 37° C. and 5% $CO_2$, followed by supernatant removal and then new medium replacement. After the cells were cultured for one day, a second transfection was performed by the same method as before. After new medium replacement, the cells were cultured under conditions of 37° C. and 5% $CO_2$. After the cells were cultured for two days, all the cells were treated with trypsin, and then harvested.

Figure 17:
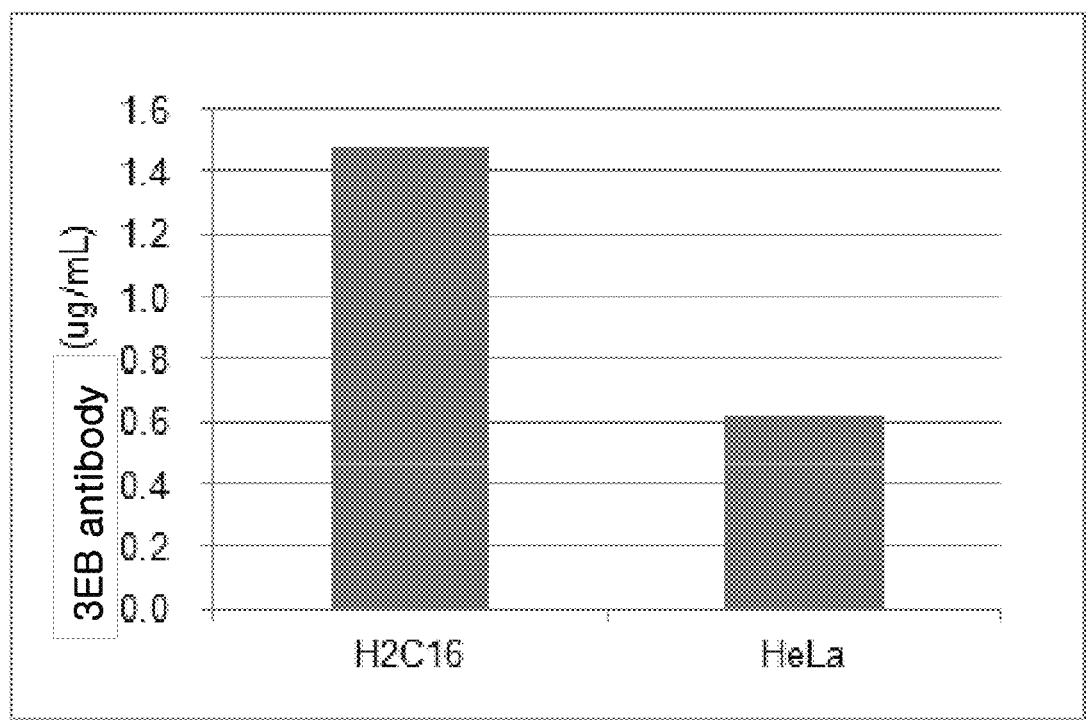
FIG. 17 shows comparison results of 3E8 antibody production capacity between H2C16 clones and HeLa cells. The 3E8 antibody contents in supernatants harvested from the respective cell lines after transfection were measured using ELISA.

The harvested cells were seeded at $4 \times 10^5$ per well in a new 6-well plate. The cells were cultured for two days under conditions of 37° C. and 5% $CO_2$, followed by supernatant removal, and then 3 ml of a new medium was added. The cells were cultured for one day under conditions of 7° C. and 5% $CO_2$, and then the supernatant was harvested. For the evaluation of 3E8 antibody content in the harvested supernatant, enzyme-linked immunosorbent assay (ELISA) was used. As a result, antibody production was confirmed in both of the two cells, but it was verified that the yield of antibodies by H2C16 clones were at least two times higher than that by HeLa cells (FIG. 17).

Having described a preferred embodiment of the present invention, it is to be understood that variants and modifications thereof falling within the spirit of the invention may become apparent to those skilled in this art, and the scope of this invention is to be determined by appended claims and their equivalents.

REFERENCES

Berk, A. J. (1986). Adenovirus promoters and E1A transactivation. Ann. Rev. genet. 20:45-79.

Brody, S. L. and Crystal, R. G. (1994). Adenovirus-mediated in vivo gene transfer. Ann NY Acad Sci 716:90-101.

Lochmuller, H., Jani, A., Huard, J., Prescott, S., Simoneau, M., Massie, B., Karpati, G. and Acsadi, G. (1994). Emergence of early region 1-containing replication-competent adenovirus in stocks of replication-defective adenovirus recombinants (ΔE1-ΔE3) during multiple passages in 293 cells. Hum. Gene Ther. 5:1485-1492

Fallaux, F. J., Kranenburg, O., Cramer, S. J., Houweling, A., VAN Ormondt, H., Hoeben, R. C. and VAN DER EB, A. J. (1996). Characterization of 911: A new helper cell line for the titration and propagation of early region 1-deleted adenoviral vector. Hum. Gene Ther. 7:215-222

Imler, J. L., Chartier, C., Dreyer, D., Dieterle, A., Saintemarie, M., Faure, T., Pavirani, A. and Mehtali, M. (1996). Novel complementation cell lines derived from human lung carcinoma A549 cells support the growth of E1-deleted adenovirus vectors. Gene Ther. 3:75-78

Murakami, P., Havenga, M., Fawaz, F., Vogels, R., Marzio, G., Pungor, E., Files, J., Do, L., Goudsmit, J. and McCaman, M. (2004). Common structure of rare replication-deficient E1-positive particles in adenoviral vector batches. J. Virol. 78:6200-6208

Gao, G. P., Engdahl, R. K., Wilson, J. M. (2000). A cell line for high-yield production of E1-deleted adenovirus vectors without the emergence of replication-competent virus. Hum. Gene Ther. 11:213-219.

Kim, J. S., Lee, S. H., Cho, Y. S., Park, K., Kim, Y. H., Lee, J. H. (2001). Development of a packaging cell line for propagation of replication-deficient adenovirus vector. Exp. Mol. Med. 33:145-149.

Tooze, J. (1981). DNA Tumor Viruses (revised). Cold Spring Habor Laboratory. Cold Spring Harbor, N.Y.

Stevens, C. W., M. Zeng, and G. J. Cerniglia. (1996). Ionizing radiation greatly improves gene transfer efficiency in mammalian cells. Hum. Gene Ther. 7:1727-1734.

Soneoka, Y., Cannon, P. M., Ramsdale, E. E., Griffiths, J. C., Romano, G., Kingsman, S. M., Kingsman, A. J. (1995). A transient three plasmid expression system for the production of high titer retroviral vectors. Nucleic Acids Res 23:628-633.

Yu, S. S., Kim, J. M. and Kim, S. (2000). High efficiency retroviral vectors that contain no viral coding sequences. Gene Ther 7:797-804.

Yu, S. S., Han, E., Hong, Y., Lee, J. T., Kim, S. and Kim, S. (2003). Construction of a retroviral vector production system with the minimum possibility of a homologous recombination. Gene Ther. 10:706-711.

Kang, H. J., Bartholomae, C. C., Paruzynski, A., Arens. A., Kim, S., Yu, S. S., Hong, Y., Joo, C W., Yoon, N K., Rhim, J W., Kim, J. G., Von Kalle, C., Schmidt, M., Kim, S. and Ahn H. S. (2011). Retroviral Gene Therapy for X-linked Chronic Granulomatous Disease: Results From Phase I/II Trial. Mol. Ther. 19:2092-2101.

Shinnick, T. M., Lerner, R. A., Sutcliffe, J. G. (1981). Nucleotide sequence of Moloney murine leukaemia virus. Nature. 293:543-548.

---

The invention claimed is:

1. An isolated cell line which is deposited under accession No. KCLRF-BP-00271.

2. An isolated cell line producing recombinant adenoviruses, the cell line comprising an adenoviral vector in the cell line of claim 1.

3. The isolated cell line of claim 2, wherein the adenoviral vector is not able to produce E1 protein, or produces inactivated E1 proteins.

4. The isolated cell line of claim 2, wherein the recombinant adenovirus is replication-incompetent.

5. A packaging system for producing recombinant adenoviruses, the system comprising: (a) the isolated cell line of claim 1; and (b) an adenoviral vector.

6. The system of claim 5, wherein the adenoviral vector is not able to produce E1 proteins, or produces inactivated E1 proteins.

7. The system of claim 5, wherein the recombinant adenovirus is replication-incompetent.

8. A method for producing target protein, the method comprising:
(a) introducing a vector including a target protein-coding nucleotide sequence into the cell line of claim 1 to obtain a transgenic cell line;
(b) culturing the transgenic cell line produced by step (a); and
(c) isolating and purifying target protein produced from the transgenic cell line.

9. The method of claim 8, wherein the target protein is selected from the group consisting of hormones, cytokines, interleukins, interleukin-binding proteins, enzymes, antibodies, growth factors, transcription factors, blood factors, vaccines, structural proteins, ligand proteins, receptors, cell surface antigens, receptor antagonists, and co-stimulating factors.

10. The method of claim 9, wherein the antibodies are antibodies against tumor-associated glycoprotein-72 (TAG-72).

* * * * *

SEQUENCE LISTING

<160> NUMBER OF SEQ ID NOS: 37

<210> SEQ ID NO 1
<211> LENGTH: 30
<212> TYPE: DNA
<213> ORGANISM: Artificial Sequence
<220> FEATURE:
<223> OTHER INFORMATION: Synthetic Construct

<400> SEQUENCE: 1
cccacgcgta tgagacatat tatctgccac          30

<210> SEQ ID NO 2
<211> LENGTH: 30
<212> TYPE: DNA
<213> ORGANISM: Artificial Sequence
<220> FEATURE:
<223> OTHER INFORMATION: Synthetic Construct

```
<400> SEQUENCE: 2
cccggatcct caatctgtat cttcatcgct                                           30

<210> SEQ ID NO 3
<211> LENGTH: 25
<212> TYPE: DNA
<213> ORGANISM: Artificial Sequence
<220> FEATURE:
<223> OTHER INFORMATION: Synthetic Construct

<400> SEQUENCE: 3
aagcttatgt gaaagacccc tcctg                                                25

<210> SEQ ID NO 4
<211> LENGTH: 42
<212> TYPE: DNA
<213> ORGANISM: Artificial Sequence
<220> FEATURE:
<223> OTHER INFORMATION: Synthetic Construct

<400> SEQUENCE: 4
ggatccgcgg gcccacgcgt attttcagac aaatacagaa ac                             42

<210> SEQ ID NO 5
<211> LENGTH: 40
<212> TYPE: DNA
<213> ORGANISM: Artificial Sequence
<220> FEATURE:
<223> OTHER INFORMATION: Synthetic Construct

<400> SEQUENCE: 5
ggatcctcga ggataaaata aaagatttta tttagtctcc                                40

<210> SEQ ID NO 6
<211> LENGTH: 26
<212> TYPE: DNA
<213> ORGANISM: Artificial Sequence
<220> FEATURE:
<223> OTHER INFORMATION: Synthetic Construct

<400> SEQUENCE: 6
gaattcaatg aaagaccccc gctgac                                               26

<210> SEQ ID NO 7
<211> LENGTH: 22
<212> TYPE: DNA
<213> ORGANISM: Artificial Sequence
<220> FEATURE:
<223> OTHER INFORMATION: Synthetic Construct

<400> SEQUENCE: 7
tgaaagaccc cacctgtagg tt                                                   22

<210> SEQ ID NO 8
<211> LENGTH: 24
<212> TYPE: DNA
<213> ORGANISM: Artificial Sequence
<220> FEATURE:
<223> OTHER INFORMATION: Synthetic Construct

<400> SEQUENCE: 8
agcatcgttc tgtgttgtct ctgt                                                 24

<210> SEQ ID NO 9
```

```
<211> LENGTH: 25
<212> TYPE: DNA
<213> ORGANISM: Artificial Sequence
<220> FEATURE:
<223> OTHER INFORMATION: Synthetic Construct

<400> SEQUENCE: 9
ttctggtagg agacgagaac ctaaa                                          25

<210> SEQ ID NO 10
<211> LENGTH: 23
<212> TYPE: DNA
<213> ORGANISM: Artificial Sequence
<220> FEATURE:
<223> OTHER INFORMATION: Synthetic Construct

<400> SEQUENCE: 10
ccacaggtcc tcatatagca aag                                            23

<210> SEQ ID NO 11
<211> LENGTH: 20
<212> TYPE: DNA
<213> ORGANISM: Artificial Sequence
<220> FEATURE:
<223> OTHER INFORMATION: Synthetic Construct

<400> SEQUENCE: 11
gtccggtttc tatgccaaac                                                20

<210> SEQ ID NO 12
<211> LENGTH: 23
<212> TYPE: DNA
<213> ORGANISM: Artificial Sequence
<220> FEATURE:
<223> OTHER INFORMATION: Synthetic Construct

<400> SEQUENCE: 12
gggtttcttc gctccattta tcc                                            23

<210> SEQ ID NO 13
<211> LENGTH: 22
<212> TYPE: DNA
<213> ORGANISM: Artificial Sequence
<220> FEATURE:
<223> OTHER INFORMATION: Synthetic Construct

<400> SEQUENCE: 13
atctgacctc atggaggctt gg                                             22

<210> SEQ ID NO 14
<211> LENGTH: 23
<212> TYPE: DNA
<213> ORGANISM: Artificial Sequence
<220> FEATURE:
<223> OTHER INFORMATION: Synthetic Construct

<400> SEQUENCE: 14
tggagttacc ctcagacagg ata                                            23

<210> SEQ ID NO 15
<211> LENGTH: 21
<212> TYPE: DNA
<213> ORGANISM: Artificial Sequence
<220> FEATURE:
<223> OTHER INFORMATION: Synthetic Construct

<400> SEQUENCE: 15
```

```
ccaaccttat cctacacggt g                                              21

<210> SEQ ID NO 16
<211> LENGTH: 21
<212> TYPE: DNA
<213> ORGANISM: Artificial Sequence
<220> FEATURE:
<223> OTHER INFORMATION: Synthetic Construct

<400> SEQUENCE: 16
gatcccatac aatggggtac c                                              21

<210> SEQ ID NO 17
<211> LENGTH: 22
<212> TYPE: DNA
<213> ORGANISM: Artificial Sequence
<220> FEATURE:
<223> OTHER INFORMATION: Synthetic Construct

<400> SEQUENCE: 17
cctctggaag cttcttgaag ac                                             22

<210> SEQ ID NO 18
<211> LENGTH: 20
<212> TYPE: DNA
<213> ORGANISM: Artificial Sequence
<220> FEATURE:
<223> OTHER INFORMATION: Synthetic Construct

<400> SEQUENCE: 18
gtcaagaagg cgatagaagg                                                20

<210> SEQ ID NO 19
<211> LENGTH: 20
<212> TYPE: DNA
<213> ORGANISM: Artificial Sequence
<220> FEATURE:
<223> OTHER INFORMATION: Synthetic Construct

<400> SEQUENCE: 19
gcttgccgaa tatcatggtg                                                20

<210> SEQ ID NO 20
<211> LENGTH: 22
<212> TYPE: DNA
<213> ORGANISM: Artificial Sequence
<220> FEATURE:
<223> OTHER INFORMATION: Synthetic Construct

<400> SEQUENCE: 20
aaagaccccc gctgacgggt ag                                             22

<210> SEQ ID NO 21
<211> LENGTH: 25
<212> TYPE: DNA
<213> ORGANISM: Artificial Sequence
<220> FEATURE:
<223> OTHER INFORMATION: Synthetic Construct

<400> SEQUENCE: 21
agctgttcca tctgttcctg acctt                                          25

<210> SEQ ID NO 22
<211> LENGTH: 20
<212> TYPE: DNA
```

```
<213> ORGANISM: Artificial Sequence
<220> FEATURE:
<223> OTHER INFORMATION: Synthetic Construct

<400> SEQUENCE: 22
gacccgggag atctgaattc                                               20

<210> SEQ ID NO 23
<211> LENGTH: 20
<212> TYPE: DNA
<213> ORGANISM: Artificial Sequence
<220> FEATURE:
<223> OTHER INFORMATION: Synthetic Construct

<400> SEQUENCE: 23
gaccttgatc tgaacttctc                                               20

<210> SEQ ID NO 24
<211> LENGTH: 21
<212> TYPE: DNA
<213> ORGANISM: Artificial Sequence
<220> FEATURE:
<223> OTHER INFORMATION: Synthetic Construct

<400> SEQUENCE: 24
gatctgaatt cagtggcaca g                                             21

<210> SEQ ID NO 25
<211> LENGTH: 21
<212> TYPE: DNA
<213> ORGANISM: Artificial Sequence
<220> FEATURE:
<223> OTHER INFORMATION: Synthetic Construct

<400> SEQUENCE: 25
ttccatgcct tgcaaaatgg c                                             21

<210> SEQ ID NO 26
<211> LENGTH: 22
<212> TYPE: DNA
<213> ORGANISM: Artificial Sequence
<220> FEATURE:
<223> OTHER INFORMATION: Synthetic Construct

<400> SEQUENCE: 26
atctgacctc atggaggctt gg                                            22

<210> SEQ ID NO 27
<211> LENGTH: 22
<212> TYPE: DNA
<213> ORGANISM: Artificial Sequence
<220> FEATURE:
<223> OTHER INFORMATION: Synthetic Construct

<400> SEQUENCE: 27
gcggacggaa gacagcagta gc                                            22

<210> SEQ ID NO 28
<211> LENGTH: 23
<212> TYPE: DNA
<213> ORGANISM: Artificial Sequence
<220> FEATURE:
<223> OTHER INFORMATION: Synthetic Construct

<400> SEQUENCE: 28
gatagatacg gaggataggg tgg                                           23
```

<210> SEQ ID NO 29
<211> LENGTH: 23
<212> TYPE: DNA
<213> ORGANISM: Artificial Sequence
<220> FEATURE:
<223> OTHER INFORMATION: Synthetic Construct

<400> SEQUENCE: 29
tggagttacc ctcagacagg ata                                          23

<210> SEQ ID NO 30
<211> LENGTH: 21
<212> TYPE: DNA
<213> ORGANISM: Artificial Sequence
<220> FEATURE:
<223> OTHER INFORMATION: Synthetic Construct

<400> SEQUENCE: 30
atgagacata ttatctgcca c                                            21

<210> SEQ ID NO 31
<211> LENGTH: 22
<212> TYPE: DNA
<213> ORGANISM: Artificial Sequence
<220> FEATURE:
<223> OTHER INFORMATION: Synthetic Construct

<400> SEQUENCE: 31
gtaagtcaat cccttcctgc ac                                           22

<210> SEQ ID NO 32
<211> LENGTH: 2950
<212> TYPE: DNA
<213> ORGANISM: Artificial Sequence
<220> FEATURE:
<223> OTHER INFORMATION: Synthetic Construct including modified
      Adenovirus E1-coding nucleotides

<400> SEQUENCE: 32
atgagacata ttatctgcca cggaggtgtt attaccgaag aaatggccgc cagtcttttg      60
gaccagctga tcgaagaggt actggctgat aatcttccac ctcctagcca ttttgaacca    120
cctacccttc acgaactgta tgatttagac gtgacggccc ccgaagatcc caacgaggag    180
gcggtttcgc agattttttcc cgactctgta atgttggcgg tgcaggaagg gattgactta    240 ctcactttttc cgccggcgcc cggttctccg gagccgcctc accttcccg gcagcccgag    300 cagccggagc agagagcctt gggtccggtt tctatgccaa accttgtacc ggaggtgatc    360
gatcttacct gccacgaggc tggctttcca cccagtgacg acgaggatga agagggtgag    420
gagtttgtgt tagattatgt ggagcacccc gggcacggtt gcaggtcttg tcattatcac    480
cggaggaata cggggacccc agatattatg tgttcgcttt gctatatgag gacctgtggc    540
atgtttgtct acagtaagtg aaaattatgg gcagtgggtg atagagtggt gggtttggtg    600
tggtaatttt ttttttaatt tttacagttt tgtggtttaa agaattttgt attgtgattt    660
ttttaaaagg tcctgtgtct gaacctgagc ctgagcccga gcagaaccg gagcctgcaa    720 gacctacccg ccgtcctaaa atggcgcctg ctatcctgag acgcccgaca tcacctgtgt    780
ctagagaatg caatagtagt acggatagct gtgactccgg tccttctaac acacctcctg    840
agatacaccc ggtggtcccg ctgtgcccca ttaaaccagt tgccgtgaga gttggtgggc    900
gtcgccaggc tgtggaatgt atcgaggact tgcttaacga gcctgggcaa ccttttggact    960

```
tgagctgtaa acgccccagg ccataaggtg taaacctgtg attgcgtgtg tggttaacgc    1020
ctttgtttgc tgaatgagtt gatgtaagtt taataaaggg tgagataatg tttaacttgc    1080
atggcgtgtt aaatggggcg gggcttaaag ggtatataat gcgccgtggg ctaatcttgg    1140
ttacatctga cctcatggag gcttgggagt gttttggaaga ttttttctgct gtgcgtaact    1200
tgctggaaca gagctctaac agtacctctt ggttttggag gtttctgtgg ggctcatccc    1260
aggcaaagtt agtctgcaga attaaggagg attacaagtg ggaatttgaa gagcttttga    1320
aatcctgtgg tgagctgttt gattctttga atctgggtca ccaggcgctt ttccaagaga    1380
aggtcatcaa gactttggat ttttccacac cggggcgcgc tgcggctgct gttgcttttt    1440
tgagttttat aaaggataaa tggagcgaag aaacccatct gagcgggggg tacctgctgg    1500
attttctggc catgcatctg tggagagcgg ttgtgagaca caagaatcgc ctgctactgt    1560
tgtcttccgt ccgcccggcg ataataccga cggaggagca gcagcagcag caggaggaag    1620
ccaggcggcg gcggcaggag cagagcccat ggaacccgag agccggcctg gaccctcggg    1680
aatgaatgtt gtacaggtgg ctgaactgta tccagaactg agacgcattt tgacaattac    1740
agaggatggg caggggctaa aggggtaaa gaggagcgg ggggcttgtg aggctacaga    1800
ggaggctagg aatctagctt ttagcttaat gaccagacac cgtcctgagt gtattacttt    1860
tcaacagatc aaggataatt gcgctaatga gcttgatctg ctggcgcaga agtattccat    1920
agagcagctg accacttact ggctgcagcc aggggatgat tttgaggagg ctattagggt    1980
atatgcaaag gtggcactta ggccagattg caagtacaag atcagcaaac ttgtaaatat    2040
caggaattgt tgctacattt ctgggaacgg ggccgaggtg gagatagata cggaggatag    2100
ggtggccttt agatgtagca tgataaatat gtggccgggg gtgcttggca tggacggggt    2160
ggttattatg aatgtaaggt ttactggccc caatttagc ggtacggttt tcctggccaa    2220
taccaacctt atcctacacg gtgtaagctt ctatgggttt aacaatacct gtgtggaagc    2280
ctggaccgat gtaagggttc ggggctgtgc cttttactgc tgctggaagg gggtggtgtg    2340
tcgccccaaa agcagggctt caattaagaa atgcctcttt gaaaggtgta ccttgggtat    2400
cctgtctgag ggtaactcca gggtgcgcca caatgtggcc tccgactgtg gttgcttcat    2460
gctagtgaaa agcgtggctg tgattaagca taacatggta tgtggcaact gcgaggacag    2520
ggcctctcag atgctgacct gctcggacgg caactgtcac ctgctgaaga ccattcacgt    2580
agccagccac tctcgcaagg cctggccagt gtttgagcat aacatactga cccgctgttc    2640
cttgcatttg ggtaacagga gggggtgtt cctaccttac caatgcaatt tgagtcacac    2700
taagatattg cttgagcccg agagcatgtc caaggtgaac ctgaacgggg tgtttgacat    2760
gaccatgaag atctggaagg tgctgaggta cgatgagacc cgcaccaggt gcagaccctg    2820
cgagtgtggc ggtaaacata ttaggaacca gcctgtgatg ctggatgtga ccgaggagct    2880
gaggcccgat cacttggtgc tggcctgcac ccgcgctgag tttggctcta gcgatgaaga    2940
tacagattga                                                          2950
```

<210> SEQ ID NO 33  
<211> LENGTH: 304  
<212> TYPE: DNA  
<213> ORGANISM: Artificial Sequence  
<220> FEATURE:  
<223> OTHER INFORMATION: Synthetic Construct including alignment sequence showing Ad-E1 sequence introduced into HeLa genome

<400> SEQUENCE: 33

```
gggaaaagc gccggagcgc ggggccgagc ggagaggctc cgggccccgc ccccatcctc    60
tggccgcgac caatgagcgc cgccgccggc tgcccccta cctccctgga cctcctgaaa   120
aacgctgccc ggggaaagtc cgggcagagc ccgagcagcg gccagggtaa cgctgtcttg   180
tggacccgca cttcccaccc gagacctctc actgagcccg agccgcgcgc gacatgagcc   240
acgggaaggg aaccgacatg ctcccggaga tcgccgccgc cgtgggcttc ctctccagcc   300
tcct                                                                304
```

```
<210> SEQ ID NO 34
<211> LENGTH: 26
<212> TYPE: DNA
<213> ORGANISM: Artificial Sequence
<220> FEATURE:
<223> OTHER INFORMATION: Synthetic Construct

<400> SEQUENCE: 34
cgggatccat ggaatggagc tgggtc                                         26

<210> SEQ ID NO 35
<211> LENGTH: 27
<212> TYPE: DNA
<213> ORGANISM: Artificial Sequence
<220> FEATURE:
<223> OTHER INFORMATION: Synthetic Construct

<400> SEQUENCE: 35
ccgctcgagt catttacccg gggacag                                        27

<210> SEQ ID NO 36
<211> LENGTH: 26
<212> TYPE: DNA
<213> ORGANISM: Artificial Sequence
<220> FEATURE:
<223> OTHER INFORMATION: Synthetic Construct

<400> SEQUENCE: 36
cgggatccat ggagacacat tctcag                                         26

<210> SEQ ID NO 37
<211> LENGTH: 28
<212> TYPE: DNA
<213> ORGANISM: Artificial Sequence
<220> FEATURE:
<223> OTHER INFORMATION: Synthetic Construct

<400> SEQUENCE: 37
ccgctcgagt taacactctc ccctgttg                                       28
```